United States Patent
Oh et al.

(10) Patent No.: US 11,786,585 B2
(45) Date of Patent: Oct. 17, 2023

(54) ANTI-IGFBP-3R ANTIBODIES AND METHODS OF TREATING AN IGFBP-3R EXPRESSING CANCER

(71) Applicant: VIRGINIA COMMONWEALTH UNIVERSITY, Richmond, VA (US)

(72) Inventors: Youngman Oh, Glen Allen, VA (US); Qing Cai, Richmond, VA (US)

(73) Assignee: Virginia Commonwealth University, Richmond, VA (US)

(*) Notice: Subject to any disclaimer, the term of this patent is extended or adjusted under 35 U.S.C. 154(b) by 0 days.

(21) Appl. No.: 17/532,397

(22) Filed: Nov. 22, 2021

(65) Prior Publication Data

US 2022/0152177 A1    May 19, 2022

Related U.S. Application Data

(63) Continuation of application No. 16/346,353, filed as application No. PCT/US2017/059244 on Oct. 31, 2017, now Pat. No. 11,179,451.

(60) Provisional application No. 62/502,917, filed on May 8, 2017, provisional application No. 62/415,620, filed on Nov. 1, 2016.

(51) Int. Cl.
| | |
|---|---|
| A61K 39/395 | (2006.01) |
| A61K 39/00 | (2006.01) |
| C07K 16/28 | (2006.01) |
| A61P 35/00 | (2006.01) |
| G01N 33/574 | (2006.01) |
| A61P 35/04 | (2006.01) |

(52) U.S. Cl.
CPC ...... *A61K 39/001102* (2018.08); *C07K 16/28* (2013.01); *A61K 2039/505* (2013.01); *A61P 35/00* (2018.01); *A61P 35/04* (2018.01); *C07K 2317/73* (2013.01); *C07K 2317/75* (2013.01); *G01N 33/57492* (2013.01); *G01N 2333/71* (2013.01); *G01N 2800/52* (2013.01)

(58) Field of Classification Search
None
See application file for complete search history.

(56) References Cited

U.S. PATENT DOCUMENTS

2014/0286966 A1* 9/2014 Oh .................... C07K 16/2869
                                                                  514/8.7

OTHER PUBLICATIONS

Oh. Endocrine 7(1): 111-113, 1997.*

* cited by examiner

*Primary Examiner* — Christine J Saoud
(74) *Attorney, Agent, or Firm* — WCF IP

(57) ABSTRACT

Insulin-like growth factor-binding protein 3 receptor (IGFBP-3R) agonists and methods of their use to treat diseases involving IGFBP-3 and IGFBP-3R are provided. The agonists may be antibodies or other molecules specific for binding to and activating IGFBP-3R. The agonists are used to treat e.g. cancer, metabolic syndrome and obstructive respiratory disorders. In addition, methods of diagnosing cancer and predicting the chance of recurrence, metastasis and/or survival by measuring the level of IGFBP-3R in tumor tissue are provided.

5 Claims, 25 Drawing Sheets

Specification includes a Sequence Listing.

1. MCF-10A
2. MCF-7
3. T47D
4. MDA-MB231
5. Hs5787T

Tumor Size

Control (IgG)

TMEM219 mAb

FIG. 11A   Control (+ PBS)
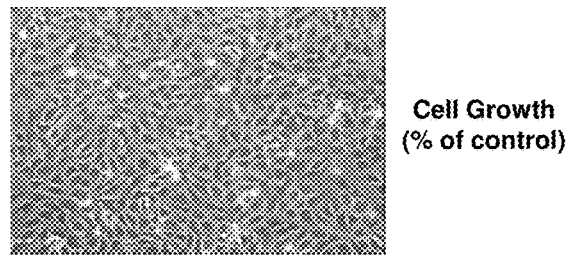
Cell Growth
(% of control)
FIG. 11B   +TMEM219 mAb1 (1µM)
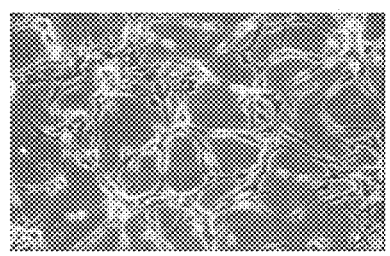
FIG. 11C   +TMEM219 mAb2 (30nM)
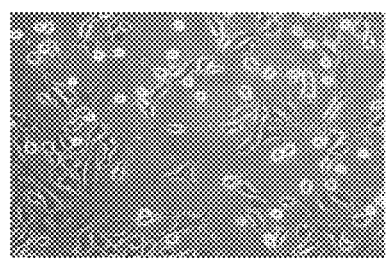
FIG. 11D
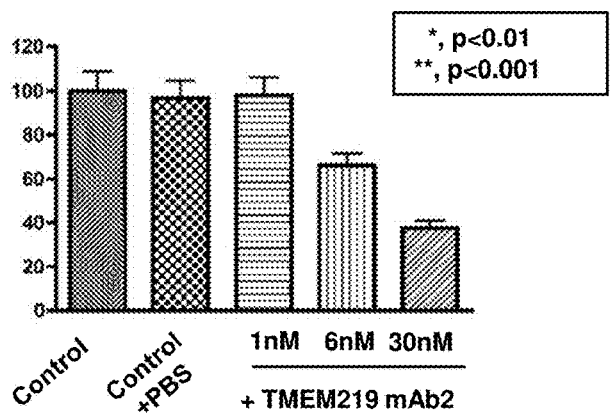
*, p<0.01
**, p<0.001
+ TMEM219 mAb2

ANTI-IGFBP-3R ANTIBODIES AND METHODS OF TREATING AN IGFBP-3R EXPRESSING CANCER

SEQUENCE LISTING

This document incorporates by reference an electronic sequence listing text file, which was electronically submitted along with this document. The text file is named 2021-11-22_02941136C1_SequenceListing.txt, is 20,309 bytes, and was created on Nov. 22, 2021.

DESCRIPTION

Background of the Invention

Field of the Invention

The invention generally relates to methods of treating diseases involving insulin-like growth factor-binding protein 3 (IGFBP-3) and its receptor, IGFBP-3R. In particular, the invention provides methods of diagnosing cancer, and treating cancer, metabolic syndrome and obstructive respiratory disorders using IGFBP-3R agonists.

Background of the Invention

The American Cancer Society estimates that almost 1.7 million new cases of cancer will be diagnosed in 2017. With respect to cancer mortality, lung cancer is by far the leading cause of cancer death among females (25%), followed by breast (14%), and colorectal (8%) cancers. Among males, lung (27%), colorectal (9%) and prostate (8%) cancers are the leading causes of cancer death. New therapy for those high mortality cancers is urgently needed. Oncology drug discovery currently suffers from a very acute paucity of selective and drug-accessible molecular targets in which to attack tumor cells.

In particular, according to the American Cancer Society, about 1 in 8 (12%) women in the US will develop invasive breast cancer (BC) during their lifetime and about 40,000 women will die from BC in 2016. In particular, triple negative breast cancer (TNBC), constituting a heterogeneous subtype of BC that lacks expression of the drug targets ER, PR and HER2, accounts for 15-20% of all diagnosed BC cases, and yet is responsible for a disproportionate number of cancer-related deaths[1]. TNBC does not respond to hormonal therapy (such as tamoxifen or aromatase inhibitors) or therapies that target HER2 receptors, such as Herceptin (trastuzumab). Current treatment mainly relies on chemo- and radiation-therapy as there are no targeted therapies specifically approved for TNBC. Despite initial responses to chemotherapy and radiation-therapy, resistance frequently and rapidly develops. Given the complexity of TNBC biology and the lack of "traditional" therapeutic targets, new targeted approaches are, therefore, urgently needed.

Metabolic syndrome is a serious health condition that is becoming more and more prevalent as frequency of obesity and sedentary lifestyles arise, and as a result of aging populations. For example, in the United States, about 34% of the population has metabolic syndrome, and the prevalence increases with age: metabolic syndrome affects about 60% of the U.S. population older than age 50. Metabolic syndrome is associated with an increased risk of several debilitating diseases, including insulin resistance, atherosclerotic cardiovascular disease (e.g., heart disease and stroke) and type 2 diabetes. The development of these diseases results in a high negative impact on the quality of life of those who are afflicted, and places a high burden on the already strained health care systems of countries. While some treatments are available for specific symptoms (e.g. drugs for high blood pressure, etc.), and while life style changes can have a positive impact, all patients do not respond equally well to medications or to the need for life style changes. It would be beneficial to have available additional medicaments to treat metabolic syndrome.

Obstructive respiratory disorders (also known as obstructive lung or pulmonary disease) is a category of respiratory disease characterized by airway obstruction. Several diseases are included in this category, including chronic obstructive pulmonary disease (COPD) and asthma. The incidence of these maladies is on the rise. For example, according to estimates from the Global Burden of Disease Study, COPD, which afflicts both smokers and non-smokers, afflicted more than 300 million people worldwide in 2013, with 250,000 annual deaths attributed to the disease. The disease burden and its financial impact is predicted to increase, e.g. due to population aging. As of 2014, it was estimated that asthma affected as many as 334 million people worldwide. It is the most common chronic disease in children and its prevalence is also rising. While there are some medications available to control symptoms, there is an ongoing need to provide additional improved methods and agents for treating these and other types of obstructive respiratory disorders.

SUMMARY OF THE INVENTION

Various features and advantages of the present invention are set forth in the description of invention that follows, and in part will be apparent from the description or may be learned by practice of the invention. The invention will be realized and attained by the compositions and methods particularly pointed out in the written description and claims hereof.

This disclosure describes a critical antitumor, anti-inflammatory signaling cascade, the IGFBP-3/IGFBP-3R axis. It has been discovered that IGFBP-3 and its receptor, IGFBP-3R play a role in several diseases, including cancer, metabolic syndrome, obstructive respiratory disorders and various inflammatory disorders. (IGFBP-3R is also known as "transmembrane protein 219" and "IGFBP-3R" and the acronym "TMEM219" may be used interchangeably herein.) For such diseases, in some aspects, it has been determined that the level of IGFBP-3 that is produced is insufficient to cause sufficient activation of IGFBP-3R (TMEM219). Therefore, the present disclosure provides agents that substitute for the natural ligand IGFBP-3. The agents are TMEM219 agonists which bind to and activate TMEM219 and can thus be used to prevent, treat or ameliorate symptoms of such diseases and/or in some cases, the recurrence of the diseases, and/or improve the prognosis (e.g. survival rate, rate of relapse, disease free survival time, etc.) of patients suffering from the diseases. In one aspect, the TMEM219 agonists are monoclonal antibodies (mAbs). Thus, this disclosure describes the therapeutic use of TMEM219 agonist mAbs to treat cancer (including breast, colon and lung cancer), metabolic syndrome, obstructive respiratory disorders, inflammatory disorders, and related diseases. In particular, TMEM219 agonistic antibodies constitute a new generation of therapeutics with a unique mechanism and target specificity for treating these disorders. The TMEM219 agonist mAbs advantageously exhibit no deleterious harmful effects (such as cell damage or cell killing) on normal, non-disease (e.g. non-tumor) cells.

In addition, with respect to cancer diagnosis, it has been discovered that a low level of expression of TMEM219 in tumor cells is indicative of a poor prognosis, e.g. an increased risk of metastasis, recurrence and/or a lower overall chance of survival. Thus, for patients with levels of expression of TMEM219 that are lower than a predetermined, corresponding reference value, an aggressive treatment regimen is typically recommended. Conversely, patients with a high level of expression of TMEM219 in tumor cells have a relatively good prognosis, with a lower risk of metastasis and recurrence and/or a higher chance of survival. Accordingly, a less aggressive (and thus less toxic) treatment regimen with fewer side effects is recommended.

It is an object of this disclosure to provide an agonist that binds to and activates TMEM219. In some aspects, the agonist is a small molecule, a peptide, a polypeptide or an antibody. In other aspects, the agonist is an antibody containing at least one complementarity determining region (CDR) selected from the group consisting of: SEQ ID NO: 15, SEQ ID NO: 17, SEQ ID NO: 19, SEQ ID NO: 21, SEQ ID NO: 23, the amino acid sequence ATS, SEQ ID NO: 25, SEQ ID NO: 27, SEQ ID NO: 29, SEQ ID NO: 31, the amino acid sequence SAS, and SEQ ID NO: 33, or a CDR that is at least 90% identical to the at least one CDR. In further aspects, the antibody comprises i) a heavy chain with an amino acid sequence that is at least 90% identical to SEQ ID NO: 1, SEQ ID NO: 3 or SEQ ID NO: 5, and/or ii) a light chain with an amino acid sequence that is at least 90% identical to SEQ ID NO: 2, SEQ ID NO: 4 or SEQ ID NO: 6. In additional aspects, i) the heavy chain is at least 90% identical to SEQ ID NO: 1 and the light chain is at least 90% identical to SEQ ID NO: 2; ii) the heavy chain is at least 90% identical to SEQ ID NO: 3 and the light chain is at least 90% identical to SEQ ID NO: 4; or iii) the heavy chain is at least 90% identical to SEQ ID NO: 5 and the light chain is at least 90% identical to SEQ ID NO: 6. In some aspects, the antibody comprises a detectable label.

The disclosure also provides a method of treating an TMEM219 expressing cancer in a patient in need thereof, comprising: administering to said patient a therapeutically effective amount of an agonist that binds to and activates TMEM219. In some aspects, the agonist is a small molecule, a peptide, a polypeptide or an antibody. In other aspects, the agonist is an antibody containing at least one complementarity determining region (CDR) selected from the group consisting of: SEQ ID NO: 15, SEQ ID NO: 17, SEQ ID NO: 19, SEQ ID NO: 21, SEQ ID NO: 23, the amino acid sequence ATS, SEQ ID NO: 25, SEQ ID NO: 27, SEQ ID NO: 29, SEQ ID NO: 31, the amino acid sequence SAS, and SEQ ID NO: 33, or a CDR that is at least 90% identical to the at least one CDR. In further aspects, the antibody comprises i) a heavy chain with an amino acid sequence that is at least 90% identical to SEQ ID NO: 1, SEQ ID NO: 3 or SEQ ID NO: 5, and/or ii) a light chain with an amino acid sequence that is at least 90% identical to SEQ ID NO: 2, SEQ ID NO: 4 or SEQ ID NO: 6. In additional aspects, i) the heavy chain is at least 90% identical to SEQ ID NO: 1 and the light chain is at least 90% identical to SEQ ID NO: 2; ii) the heavy chain is at least 90% identical to SEQ ID NO: 3 and the light chain is at least 90% identical to SEQ ID NO: 4; or iii) the heavy chain is at least 90% identical to SEQ ID NO: 5 and the light chain is at least 90% identical to SEQ ID NO: 6. In some aspects, the cancer is breast cancer, colon cancer, lung cancer, ovarian cancer, pancreatic cancer, liver cancer or leukemia.

The disclosure also provides a method of treating insulin resistance in a patient in need thereof, comprising: administering to said patient a therapeutically effective amount of an agonist that binds to and activates TMEM219. In some aspects, the agonist is a small molecule, a peptide, a polypeptide or an antibody. In other aspects, the agonist is an antibody containing at least one complementarity determining region (CDR) selected from the group consisting of: SEQ ID NO: 15, SEQ ID NO: 17, SEQ ID NO: 19, SEQ ID NO: 21, SEQ ID NO: 23, the amino acid sequence ATS, SEQ ID NO: 25, SEQ ID NO: 27, SEQ ID NO: 29, SEQ ID NO: 31, the amino acid sequence SAS, and SEQ ID NO: 33, or a CDR that is at least 90% identical to the at least one CDR. In further aspects, the antibody comprises i) a heavy chain with an amino acid sequence that is at least 90% identical to SEQ ID NO: 1, SEQ ID NO: 3 or SEQ ID NO: 5, and/or ii) a light chain with an amino acid sequence that is at least 90% identical to SEQ ID NO: 2, SEQ ID NO: 4 or SEQ ID NO: 6. In additional aspects, i) the heavy chain is at least 90% identical to SEQ ID NO: 1 and the light chain is at least 90% identical to SEQ ID NO: 2; ii) the heavy chain is at least 90% identical to SEQ ID NO: 3 and the light chain is at least 90% identical to SEQ ID NO: 4; or iii) the heavy chain is at least 90% identical to SEQ ID NO: 5 and the light chain is at least 90% identical to SEQ ID NO: 6.

The disclosure further provides a method of treating an inflammatory disorder in a patient in need thereof, comprising: administering to said patient a therapeutically effective amount of an agonist that binds to and activates TMEM219. In some aspects, the agonist is a small molecule, a peptide, a polypeptide or an antibody. In other aspects, the agonist is an antibody containing at least one complementarity determining region (CDR) selected from the group consisting of: SEQ ID NO: 15, SEQ ID NO: 17, SEQ ID NO: 19, SEQ ID NO: 21, SEQ ID NO: 23, the amino acid sequence ATS, SEQ ID NO: 25, SEQ ID NO: 27, SEQ ID NO: 29, SEQ ID NO: 31, the amino acid sequence SAS, and SEQ ID NO: 33, or a CDR that is at least 90% identical to the at least one CDR. In further aspects, the antibody comprises i) a heavy chain with an amino acid sequence that is at least 90% identical to SEQ ID NO: 1, SEQ ID NO: 3 or SEQ ID NO: 5, and/or ii) a light chain with an amino acid sequence that is at least 90% identical to SEQ ID NO: 2, SEQ ID NO: 4 or SEQ ID NO: 6. In additional aspects, i) the heavy chain is at least 90% identical to SEQ ID NO: 1 and the light chain is at least 90% identical to SEQ ID NO: 2; ii) the heavy chain is at least 90% identical to SEQ ID NO: 3 and the light chain is at least 90% identical to SEQ ID NO: 4; or iii) the heavy chain is at least 90% identical to SEQ ID NO: 5 and the light chain is at least 90% identical to SEQ ID NO: 6. In some aspects, the antibody comprises a detectable label. In some aspects, the inflammatory disorder is selected from the group consisting of ulcerative colitis, colitis, Crohn's disease, atherosclerosis, chronic peptic ulcer, chronic obstructive lung disease, idiopathic pulmonary fibrosis, tuberculosis, arthritis, chronic sinusitis, asthma, hepatitis, ankylosing spondylitis, liver fibrosis, non-alcoholic steatohepatisis or chronic periodontitis. In additional aspects, the arthritis is osteoarthritis, rheumatoid arthritis (RA), and psoriatic arthritis.

The disclosure also provides a method of determining a prognosis of a subject with cancer and treating the subject accordingly, comprising, i) measuring a level of TMEM219 expression in a tumor sample from the subject ii) comparing the level of TMEM219 expression obtained in step i) with a corresponding reference level of TMEM219 expression; and iii) if the level of TMEM219 expression is the same or lower than the corresponding reference level of TMEM219 expression, then iv) concluding that the patient has a poor prognosis and providing an aggressive anti-cancer treatment to the patient; Or v) if the level of TMEM219 expression is higher than the corresponding reference level of TMEM219 expression, then iv) concluding that the patient has a good prognosis and providing a less aggressive anti-cancer treatment to the patient. In some aspects, the cancer is breast cancer, colon cancer, lung cancer, ovarian cancer, pancreatic cancer, liver cancer or leukemia. In additional aspects, the prognosis includes one or more of risk of recurrence of the cancer in the patient, risk of metastasis, overall survival of the patient and prediction of the benefit of chemotherapy for the patient.

BRIEF DESCRIPTION OF THE DRAWINGS

FIG. 11A-E. Growth Inhibitory Effects of TMEM219 agonist mAbs in lung cancer cells (BEAS2B-NNKA) but not in normal lung epithelial cells (BEAS2B). Upper panel, NKA cells were grown up to 40% confluency; A, control; B, treated with 1 mM mAb #1 (#245) or C, 30 nM mAb #(#274) for 3 days. Similarly BEAS2B-NNKA lung cancer (D) and normal lung epithelial cells (E) were treated with 1-100 nM TMEM219 agonist mAb #2 (#274) for 3 days and live cells were counted using the TC20 automated cell counter. n=3 in duplicate.

DETAILED DESCRIPTION

Figure 1A:
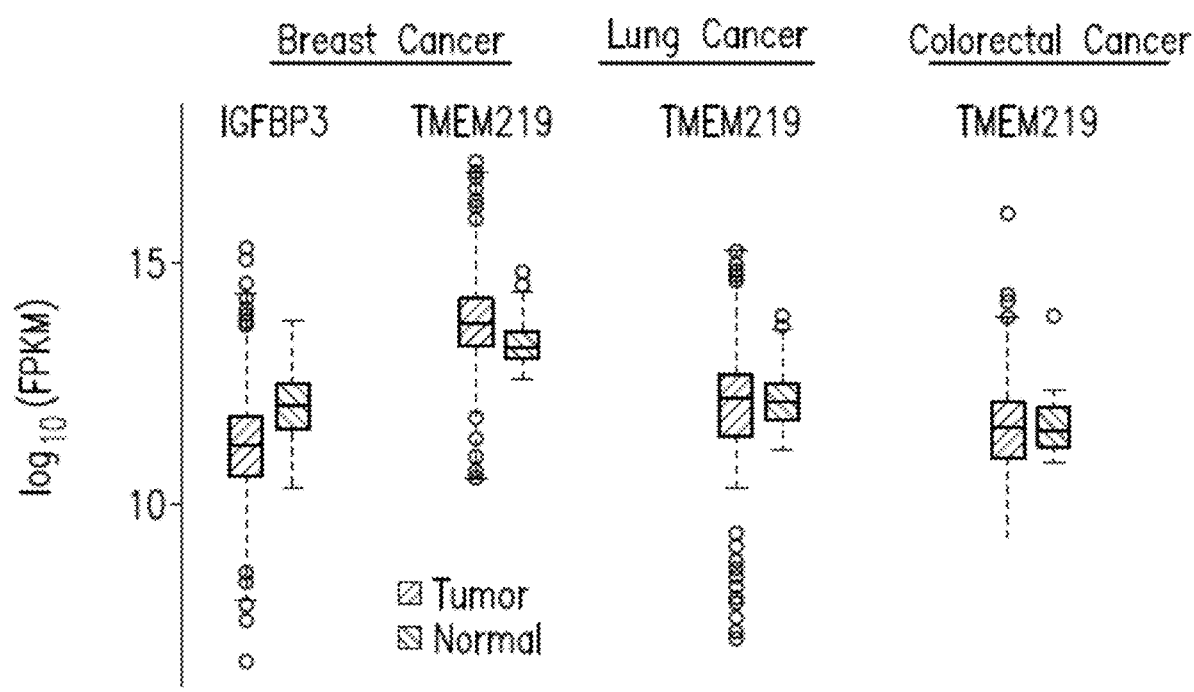
FIG. 1A and B. IGFBP3 and TMEM219 (IGFBP-3R) gene expression level in human cancer. A, CellX tool5 was used to mine publically available breast, colorectal and lung cancer gene expression data from TCGA. B, RNA sequencing data analysis of TMEM219 expression in hepatocellular carcinoma, triple negative breast cancer (TNBC), non-small cell lung carcinoma (NSCLC), colorectal, ovarian, pancreatic cancer using the Champions TumorGraft Database provided by Champions Oncology, Inc (Hackensack, N.J.).

The present disclosure describes therapeutic agents and methods of their use to treat diseases involving IGFBP-3 and its receptor, IGFBP-3R, e.g. diseases and conditions caused by abnormal functioning of IGFBP-3 and IGFBP-3R. For example, in the case of diseases caused by a lack of IGFBP-3R activation (e.g. by a lack of production or transport of IGFBP-3) agents that bind to and activate IGFBP-3R (i.e. IGRBP-3R agonists) are used as IGFBP-3 substitutes. As such, they are used to treat or ameliorate symptoms of cancer, metabolic syndrome, obstructive respiratory disorders, certain inflammatory diseases, and related disorders. In addition, the level of expression of IGFBP-3R in tumor cells is used as an indicator of the prognosis of a cancer patient, with low levels indicating a poor prognosis and high levels indicating a relatively good prognosis. This type of assessment allows medical practitioners to tailor recommended cancer treatment regimens on a patient by patient basis.

By "IGFBP-3R" or "TMEM219" refers to the Homo sapiens (human) protein that acts as the receptor for human "insulin-like growth factor-binding protein 3" or "IGFBP-3". The receptor is also known as "transmembrane protein 219" and is encoded by the TMEM219 gene (gene ID 124446 in the NCBI database).

By "agonist" we mean a chemical (compound, substance, etc.) that binds to a receptor and activates the receptor to produce a biological response. In some aspects, the agonists are monoclonal antibodies (mAbs) specific for binding to the receptor "IGFBP-3R". Upon binding, the mAbs activate the receptor, i.e. its biological activity is elicited, increased, etc., compared to the level of activation when no agonist or natural ligand is bound.

A "therapeutically effective amount" of a compound is an amount that is sufficient to treat or prevent or ameliorate (lessen) at least one symptom of a disease.

By "treat" or "treating" a disease, we mean that, in a treated individual, one or more unwanted symptoms of the disease is/are eliminated (i.e. the patient is cured), or lessened, and/or the time interval during which the symptoms are present is shortened, and/or onset of symptoms is delayed, compared to an untreated individual.

"Prevention" or "preventing" refers to stopping or averting (warding off, etc.) the occurrence of a disease or a disease aspect or symptom before it occurs, e.g. before evidence of the disease, symptom, etc. is detectable or measurable.

"VH CDR" refers to a heavy chain variable domain complementarity determining region (CDR) of an antibody. "LH CDR" refers to a light chain variable domain CDR of an antibody. There are three CDRs (CDR1, CDR2 and CDR3), arranged non-consecutively, on the amino acid sequence of a variable domain of an antigen receptor. Since the antigen receptors are typically composed of two variable domains (on two different polypeptide chains, one heavy chain and one light chain), there are six CDRs for each antigen receptor that can collectively come into contact with the antigen. A single antibody molecule has two antigen receptors and therefore contains a total of twelve CDRs, although sixty CDRs are found on a pentameric IgM molecule.

The Agonists

The agonists described herein activate the IGFBP-3R. In some aspects, such molecules bind to the receptor, for example, at the IGFBP-3 binding site which is described below, specifically or selectively. The agonists may be of any of the many known types of molecules which bind to receptors, for example small molecule drugs, antibodies, etc. Disclosed herein are monoclonal antibodies (mAbs) which are agonists or IGFBP-3, as well as CDRs contained within the antibodies. While the mAbs may be used to deliver the CDRs to the receptor (i.e. antibodies may be used to mediate contact between one or more CDRs and the receptor binding site) other molecules which contain one or more of the CDRs may also be used to do so, e.g. peptides and polypeptides which comprise one or more CDRs. Such peptides and polypeptides may be protected to decrease proteolysis and increase bioavailability, e.g. by including "non-natural" or non-cleavable amino acids (e.g. D amino acids, norleucine norvaline, ornithine, s-benzyl cysteine, etc.) in the peptide chain, or by incorporating N-acyl groups, reduced peptide bonds, etc., by amidating the COO⁻ terminus, by cyclization, PEGylation or glycosylation, etc. Alternatively, the agonist may be a small molecule drug which fits the receptor binding site and binds sufficiently to activate the receptor. By "small molecule drug" we mean an organic compound that is of a low molecular weight (<900 daltons) and which has a size on the order of 1 nm. Such small molecules typically bind to target receptors via one or more of electrostatic bonding, hydrogen bonding, and/or van der Waals/London dispersion forces. In some aspects, the agonists that are not antibodies bind to or within residues 116-125 of IGFBP-3R, the amino acid sequence of which is GLKGSSAGQL (SEQ ID NO: 13), as described below for the monoclonal antibodies described herein.

In some aspects, the IGFBP-3R agonists that are utilized in the practice of the present invention are monoclonal antibodies (mAbs) specific for binding to and activating IGFBP-3R. Generally, functional studies (see FIGS. 5, 11 and 13) indicate the ED50 (effective dose, causing 50% of maximum effect for the measured biological effects in cells receiving the drug) is around 20 nM. Thus, the mAbs generally exhibit an ED50 in the range of from about 1-100 nM, e.g. about 5 to 50 nM such as about 5, 10, 15, 20, 25, 30, 35, 40, 45, or 50 nM or more.

The mAbs may or may not bind to the exact same residues that are bound by the natural ligand; however, they bind sufficiently to activate the receptor. In some aspects, the antibodies bind to the same site at which the ligand IGFBP-3 binds. Whatever the exact position of binding, the mAbs stand in for/make up for the lack of natural ligand binding and once bound, they activate the receptor. In some aspects, the mAbs bind, for example, to portions of IGFBP-3R which are accessible and not buried in the membrane, e.g. within residues 1-197 of IGFBP-3R. Further, in some aspects, the mAbs bind to or within residues 116-125 of IGFBP-3R, the amino acid sequence of which is GLKGSSAGQL (SEQ ID NO: 13). In other words, in some aspects, the mAbs bind to at least 1, 2, 3, 4, 5, 6, 7, 8, or 9 consecutive amino acids within SEQ ID NO: 13, or to all 10 amino acids of SEQ ID NO:13. In yet other aspects, the mAbs bind to from 1-9 amino acids which are not consecutive in sequence, i.e. one or more (e.g. about 1-9) amino acids within this sequence do not bind directly to the mAb. Binding to the mAbs is generally non-covalent, e.g. via one or more of electrostatic bonding, hydrogen bonding, and/or van der Waals/London dispersion forces.

Exemplary mAbs are described herein. Those of skill in the art will recognize that the invention is not limited to the use of mAbs with the exact sequences disclosed herein. For example, conservative and/or non-conservative amino acid substitutions may be made in the sequences as long as the resulting mAbs retain the ability to bind to and act as agonists of IGFBP-3R. Such variants generally have at least about 50% identity to the sequences disclosed herein, e.g. at least about 50, 55, 60, 65, 70, 75, 80, 85, 90, 91, 92, 93, 94, 95, 96, 97, 98 or 99% identity to the disclosed sequences. In addition, antibodies may be designed and produced which contain one or more complementarity-determining regions (CDRs) of the antibodies described herein, i.e. they contain at least one paratope or antigen-binding region as described herein (such as at least one CDR), but contain different non-CDR sequences. Other variations include but are not limited to: human, humanized, or chimeric antibodies, antibody fragments that bind IGFBP-3R (e.g. human IGFBP-3R), a Fab', a F(ab')2, a F(ab')3, a monovalent scFv, a bivalent scFv, a single domain antibody, etc. The antibodies may be IgG, IgM, or IgA antibodies or antigen binding fragments thereof. In addition, the antibodies may be labeled with a detectable label as described in detail below, or may be otherwise modified, e.g. by glycosylation. All such variants are encompassed by the invention, so long as the variant binds to IGFBP-3R and acts as an agonist of IGFBP-3R.

In some aspects, the agonist is an antibody designated TMEM219 #245, TMEM219 #274 or TMEM219 #274-hIgG1 chimera. The latter is a human IgG1 chimera of TMEM219 #274. Tables 1-6 show the CDR sequences of heavy and light chains of TMEM219 #245, TMEM219 #274 and TMEM219 #274-hIgG1 chimera. To calculate the % identity shown in the Tables, TMEM219 #245 was compared to the germline IGHV9 gene sequence for the heavy chain CDRs and to the IGKV9 gene sequence for the light chain CDRs whereas TMEM219 #274 heavy chain CDRs and light chain CDRs were compared to the IGHV9 and IGKV6 gene sequences, respectively. It is noted that the CDR sequences of TMEM219 #274-hIgG1 chimera are the same as those of TMEM219 #274. It is also noted that, in an antibody, the CDRs may be denominated a first, second, third, etc. antibody as required for clarity.

TABLE 1

| | | | | | | | Identity(%) compared | |
| --- | --- | --- | --- | --- | --- | --- | --- | --- |
| CDR sequences of TMEM219#245, VHDJH heavy chain (IgG2a) | | | | | | | | |
| | From | To | Length | Matches | Mismatches | to IGHV9 gene | Sequences | |
| CDR1-IMGT | 70 | 93 | 24 | 22 | 2 | 91.7 | DNA: GGG TTT ACC TTC ACA TAC TAT GGA (SEQ ID NO: 14) Protein: G F T F T Y Y G (SEQ ID NO: 15) | |
| CDR2-IMGT | 145 | 168 | 24 | 24 | 0 | 100 | DNA: ATA AAC ACC TAC ACT GGA GAG CCA (SEQ ID NO: 16) Protein: I N T Y T G E P (SEQ ID NO: 17) | |
| CDR3-MGT germline | 283 | 288 | 6 | 6 | 0 | 100 | DNA: GCA AGA GGG CGT ACG GTA GTG GGC TTT GAC TCT (SEQ ID NO: 18) Protein: A R G R T V V G F D S (SEQ ID NO: 19) | |

TABLE 2

CDR sequences of TMEM219#245, VKJK light chain

| | From | To | Length | Matches | Mis-matches | Identity(%) Compared to IGKV9 gene | Sequences |
|---|---|---|---|---|---|---|---|
| CDR1-IMGT | 79 | 96 | 18 | 18 | 0 | 100 | DNA: CAG GAC ATT GGT AGT AGC (SEQ ID NO: 20) Protein: Q D I G S S (SEQ ID NO: 21) |
| CDR2-IMGT | 148 | 156 | 9 | 9 | 0 | 100 | DNA: GCC ACA TCC Protein: A T S |
| CDR3-MGT germ-line | 265 | 284 | 20 | 20 | 0 | 100 | DNA: CTA CAA TAT GCT AGT TCT CCG TAC ACG (SEQ ID NO: 22) Protein: L Q Y A S S P (SEQ ID NO: 23) |

TABLE 3

CDR sequences of TMEM219#274, VHDJH heavy chain (IgG3)

| | From | To | Length | Matches | Mis-matches | Identity(%) Compared to IGHV9 gene | Sequences |
|---|---|---|---|---|---|---|---|
| CDR1-IMGT | 76 | 99 | 24 | 23 | 1 | 95.8 | DNA: GGG TAT ACT TTC ACA AAC TAT GGA (SEQ ID NO: 24) Protein: G Y T F T N Y G (SEQ ID NO: 25) |
| CDR2-IMGT | 151 | 174 | 24 | 21 | 3 | 87.5 | DNA: ATA AAC ACC TAC ACC AGA GAG ACA (SEQ ID NO: 26) Protein: I N T Y T R E T (SEQ ID NO: 27) |
| CDR3-MGT germ-line | 289 | 294 | 6 | 6 | 0 | 100 | DNA: GCA AGA GGG TCT ACG ATG TAT GGT CTG GAC AAG (SEQ ID NO: 28) Protein: A R G S T M Y G L D K (SEQ ID NO: 29) |

TABLE 4

CDR sequences of TMEM219#274, VKJK light chain

| | From | To | Length | Matches | Mis-matches | Identity(%) Compared to IgKV6 gene | Sequences |
|---|---|---|---|---|---|---|---|
| CDR1-IMGT | 79 | 96 | 18 | 18 | 0 | 100 | DNA: CAG AAT GTG GGT ACT AAT (SEQ ID NO: 30) Protein: Q N V G T N (SEQ ID NO: 31) |

TABLE 4-continued

CDR sequences of TMEM219#274, VKJK light chain

|  | From | To | Length | Matches | Mis-matches | Identity(%) Compared to IgKV6 gene | Sequences |
|---|---|---|---|---|---|---|---|
| CDR2-IMGT | 148 | 156 | 9 | 9 | 0 | 100 | DNA: TCG GCA TCC<br>Protein: S A S |
| CDR3-MGT germ-line | 265 | 287 | 23 | 22 | 1 | 95.7 | DNA: CAC CAA TAT AAC AGC TAT CCT CTC ACG (SEQ ID NO: 32)<br>Protein: H Q Y N S Y P L T (SEQ ID NO: 33) |

TABLE 5

TMEM219 #274-hIgG1 chimera CDR sequences (same as those of TMEM219@274

|  | Heavy chain | κ Light chain |
|---|---|---|
| CDR1-IMGT | Protein: G Y T F T N Y G (SEQ ID NO: 25) | Protein: Q N V G T N (SEQ ID NO: 31) |
| CDR2-IMGT | Protein: I N T Y T R E T (SEQ ID NO: 27) | Protein: S A S |
| CDR3-MGT germ-line | Protein: A R G S T M Y G L D K (SEQ ID NO: 29) | Protein: H Q Y N S Y P L T (SEQ ID NO: 33) |

In some aspects, the antibody comprises one or more of the CDRs of antibody TMEM219 mAb #1 (#245) as follows: (a) a VH CDR at least 90% identical to SEQ ID NO: 15; (b) a VH CDR at least 90% identical to SEQ ID NO: 17; (c) a VH CDR at least 90% identical to SEQ ID NO: 19; (d) a VL CDR at least 90% identical to VL CDR1 of SEQ ID NO: 21; (e) a VL CDR at least 90% identical to SEQ ID NO: 23; and (f) a VL CDR at least 90% identical to the sequence ATS. That is, the sequence is about 90, 91, 92, 93, 94, 95, 96, 97, 98, 99 or even 100% identical to the indicated sequence.

In other aspects, the antibody comprises one or more of the CDRs of antibody TMEM219 mAb #2 (#274) as follows: (a) a VH CDR at least 90% identical to SEQ ID NO: 25; (b) a VH CDR at least 90% identical to SEQ ID NO: 27; (c) a VH CDR at least 90% identical to SEQ ID NO: 29; (d) a VL CDR at least 90% identical to VL CDR1 of SEQ ID NO: 31; (e) a VL CDR at least 90% identical to the sequence SAS; and (f) a VL CDR at least 90% identical to SEQ ID NO: 33. That is, the sequence is about 90, 91, 92, 93, 94, 95, 96, 97, 98, 99 or even 100% identical to the indicated sequence.

In some aspects, the antibody comprises one or more of the CDRs of antibody TMEM219 #274-human IgG1 (#274-hIgG1) chimera as follows: (a) a VH CDR at least 90% identical to SEQ ID NO: 25; (b) a VH CDR at least 90% identical to SEQ ID NO: 27; (c) a VH CDR at least 90% identical to SEQ ID NO: 29; (d) a VL CDR at least 90% identical to VL CDR1 of SEQ ID NO: 31; (e) a VL CDR at least 90% identical to the sequence SAS; and (f) a VL CDR at least 90% identical to SEQ ID NO: 33. That is, the sequence is about 90, 91, 92, 93, 94, 95, 96, 97, 98, 99 or even 100% identical to the indicated sequence.

Those of skill in the art will recognize that suitable antibodies for use in the methods described herein are obtainable from hybridomas using technology that is known in the art. Alternatively, the antibodies may be made by recombinant technology, e.g. by cell culture or bacterial culture, as is well-known in the art, or even synthetically via chemical peptide synthesis.

In some aspects, the antibodies are used to treat diseases such as cancer. In these aspects, the antibodies may be modified to include other effector molecules. Non-limiting examples of effector molecules that can be attached to antibodies include toxins, therapeutic enzymes, antibiotics, radio-labeled nucleotides and the like. As is known in the art, linking molecules may be used to join the antibody to the effector molecule. Such effectors may be especially useful when the disease that is treated is cancer.

In addition, the encoding nucleic acids need not be identical to those described herein, e.g. due to the redundancy of the genetic code. In general, encoding sequences will generate the antibodies described herein, and may or may not be codon optimized for production in a particular way, e.g. in plant, mammalian or bacterial host cells. Nucleic acids encompassed by the invention include but are not limited to DNA and RNA, and sequences that are at least about 90% homologous to the sequences disclosed herein (e.g. about 90, 91, 92, 93, 94, 95, 96, 97, 98, 99 or even 100% homologous). Further, the invention encompasses vectors (plasmids, cosmids, viral vectors, etc.) which include the encoding nucleic acids sequences, and cells which contain the nucleic acid sequences and/or the vectors.

Compositions

The invention also comprises compositions comprising one or more of the agonists (e.g. antibodies) described herein. Those of skill in the art will recognize that the components in the compositions will vary depending on whether the antibodies are used in diagnostic methods or in treatment methods, whether or not they are labeled, etc.

When used for treatment methods, the compounds described herein are generally delivered (administered) as a pharmaceutical composition/formulation. The compositions generally include one or more substantially purified antibodies as described herein, and a pharmacologically suitable (physiologically compatible) carrier, which may be aqueous or oil-based. In some aspects, such compositions are prepared as liquid solutions or suspensions, or as solid forms such as tablets, pills, powders and the like. Solid forms suitable for solution in, or suspension in, liquids prior to administration are also contemplated (e.g. lyophilized forms of the compounds), as are emulsified preparations. In some aspects, the liquid formulations are aqueous or oil-based suspensions or solutions. In some aspects, the active ingredients are mixed with excipients which are pharmaceutically acceptable and compatible with the active ingredients, e.g. pharmaceutically acceptable salts. Suitable excipients include, for example, water, saline, dextrose, glycerol, ethanol and the like, or combinations thereof. In addition, the composition may contain minor amounts of auxiliary substances such as wetting or emulsifying agents, pH buffering agents, preservatives, and the like. If it is desired to administer an oral form of the composition, various thickeners, flavorings, diluents, emulsifiers, dispersing aids or binders and the like are added. The composition of the present invention may contain any such additional ingredients so as to provide the composition in a form suitable for administration. The final amount of antibody in the formulations varies, but is generally from about 1-99%. Still other suitable formulations for use in the present invention are found, for example in Remington's Pharmaceutical Sciences, 22nd ed. (2012; eds. Allen, Adejarem Desselle and Felton).

Some examples of materials which can serve as pharmaceutically acceptable carriers include, but are not limited to, ion exchangers, alumina, aluminum stearate, lecithin, serum proteins (such as human serum albumin), buffer substances (such as twin 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

"Pharmaceutically acceptable salts" refers to the relatively non-toxic, inorganic and organic acid addition salts, and base addition salts, of compounds of the present invention. These: salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-.beta.-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts, and the like. See, for example S. M. Berge, et al., "Pharmaceutical Salts," J. Pharm. Sci., 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use. ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

The compositions may be administered in vivo by any suitable route including but not limited to: inoculation or injection (e.g. intravenous, intraperitoneal, intramuscular, subcutaneous, intra-aural, intraarticular, intramammary, intratumoral, and the like), by topical application and by absorption through epithelial or mucocutaneous linings (e.g., nasal, oral, vaginal, rectal, gastrointestinal mucosa, and the like). Other suitable means include but are not limited to: inhalation (e.g. as a mist or spray), orally (e.g. as a pill, capsule, liquid, etc.), intravaginally, intranasally, rectally, etc. In preferred embodiments, the mode of administration is oral or by injection. In addition, the compositions may be administered in conjunction with other treatment modalities such as substances that boost the immune system, various chemotherapeutic agents, antibiotic agents, and the like.

The dose of antibody that is administered varies according to factors such as the exact type of disease, the method of administration, overall health of the patient, etc., but is generally in the range of from about 1-100 mg/kg, or from about 2.5–75 mg/kg or 5-50 mg/kg of body weight, including all whole number and decimal fractions thereof lying within the ranges.

Diagnostics

In some aspects, the antibodies described herein are used to detect the expression level of IGFBP-3R (TMEM219) to diagnose and prognose cancer. In such cases, the antibodies may be labeled with a detectable reporter molecule. A reporter molecule is defined herein as any moiety that may be detected using an assay. Non-limiting examples of reporter molecules that may be conjugated to antibodies include but are not limited to enzymes, radiolabels, haptens, fluorescent labels, phosphorescent molecules, chemiluminescent molecules, chromophores, luminescent molecules, photoaffinity molecules, secondary or tertiary antibodies, and colored particles or ligands, such as biotin. As is known in the art, linking molecules may be used to join the antibody to the reporter molecule. In further aspects, the antibodies may be immobilized on a solid support for use in an assay, e.g. on beads, in the wells of an assay plate, etc.

Compositions for diagnostic agents can include any of the components listed above for compositions, but less care needs to be taken to promote physiological compatibility. Generally the assay solution is aqueous based and is buffered, and may contain preservatives, various salts, etc. Kits comprising a container comprising the antibodies are also provided. The kits may contain other reagents (e.g. reagents to detect a detectable label), directions for use, positive and/or negative reference standards, etc.

Diagnostic assays generally involve obtaining a biological sample of interest from a subject (e.g. a blood or plasma sample, a tissue sample, a biopsy sample, etc.) and exposing the sample to one or more antibodies as disclosed herein under conditions which allow binding to the antibody to a target molecule of interest, e.g. the TMEM219 molecule. The antibodies generally comprise a detectable label, which after binding to the molecule of interest, is detected by methods known in the art and specific for each different label, and the amount of labeled antibody is correlated to the amount of the molecule of interest that is present in the sample, e.g. by the use of one or more reference values, as described below.

Prognosing and Treating Cancer

The methods described herein are used to diagnose cancer and/or to confirm a cancer diagnosis and/or to determine the prognosis of a patient with cancer, e.g. to predict one or more of metastatic potential, chances of recurrence and prospects for survival. In some aspects, the patients treatment is tailored (modified, selected, etc.) according to the results of the method. Cancers which may be assessed in this manner include but are not limited to breast cancer, colon cancer, lung cancer, ovarian cancer, pancreatic cancer, liver cancer and leukemia.

The invention thus provides methods of determining the prognosis of a subject with cancer and treating the subject accordingly, comprising: i) measuring a level of TMEM219 expression in a tumor sample (e.g. a biopsy sample) from the subject; ii) comparing the level of TMEM219 expression obtained in step i) with a reference level of TMEM219 expression; and iii) if the level of TMEM219 expression is the same or lower than the reference level of TMEM219 expression, then, iv) concluding that the patient has a poor prognosis and providing aggressive anti-cancer treatment to the patient, examples of which include combination therapy with TMEM219 agonist antibody and chemotherapy, radiotherapy, adjuvant therapy or hormone therapy or v) if the level of TMEM219 expression is higher than the reference level of TMEM219 expression, then iv) concluding that the patient has a good prognosis and providing less aggressive anti-cancer treatment to the patient, examples of which include combination therapy with TMEM219 agonist antibody and chemotherapy or radiotherapy. The level of TMEM219 expression in the tumor sample is determined by any of many known methods for determining protein expression, including but not limited to: measuring the protein per se e.g. using antibodies (which are generally labelled with a detectable label), etc.; measuring mRNA encoding the protein, e.g. via PCR using primers (which are generally labelled with a detectable label), etc.

Once the level of TMEM219 expression has been measured, the level is compared to at least one reference value. Establishing suitable reference values is known in the art. Generally, such a value is established by measuring a substance of interest (protein, mRNA, etc.) that is indicative of the amount of TMEM219 expression in one or more appropriate control groups of comparable individuals who are healthy, i.e. in the present case, individuals who do not have cancer. However, additional reference values may also be used, e.g. reference values established using tissue from other cancer patients with high and/or low is levels of TMEM219 expression, and reference values based on cancerous and/or non-cancerous tissue from the patient him/herself. Reference values may be obtained from patients with cancer or who have had cancer and who have or have not been treated for cancer, etc. e.g. patients in remission, those being actively treated for cancer, and the like. Controls may or may not be matched with respect to e.g. age, gender, ethnicity, overall health, life style, etc., as appropriate.

As used herein, a level of TMEM219 expression that is "equal to", "higher than" or "lower than" a reference value is: the same as the reference value (e.g. +/−about 5-10% of the reference value), or higher than the reference value e.g. at least about 10% or more higher than the reference value, or lower than the reference value e.g. at least about 10% or more lower than the reference value, respectively. In some aspects, an amount of mRNA that is "equal to" is within +/−about 1-5% of Log [Fragments Per Kilobase of transcript per Million (RPKM)+1] 6.06 for colorectal cancer, 5.80 for ovarian cancer, 5.93 for pancreatic cancer, 5.43 for hepatocellular carcinoma, 5.77 for NSCLC and 5.91 for TNBC. A "higher" level is a value that is at least about 5% greater that the above mentioned Log(RPKM+1) values. A "lower" level is a value that is at least about 5% less than the above mentioned Log(RPKM+1) values. For example, for colorectal cancer, an "equal" value falls within a range of from about 6.363 to about 5.757, a high value exceeds 6.363 and a low value is below 5.757. Alternatively, the "equal" range may be within 1-10% of the indicated values, low values are at least 1-10% below and high values are at least 1-10% above the indicated reference values. Patients that are found to have TMEM219 expression levels equal to or lower than a suitable corresponding reference value are considered to have a poor prognosis, e.g. a high likelihood of one or more of metastasis, recurrence, and low overall survival. Such patients are treated with an aggressive treatment regimen, as described below. Patients that are found to have TMEM219 expression levels higher than the reference value are considered to have a good prognosis, e.g. a low likelihood of one or more of metastasis, recurrence, and overall high expectation of survival. Such patients are treated with a less aggressive treatment regimen, as described below, and can avoid suffering the unwanted, detrimental side effects of aggressive treatment. Such patients may in fact need no therapy (or no further therapy, if they have already been treated) but may benefit from monitoring the level of TMEM219 expression on an ongoing basis.

It is within the purview of the skilled medical practitioner to select an appropriate therapeutic regimen. Therapeutic regimens may be comprised of the use of cancer chemotherapeutic agents and/or radiation and/or surgery. A cancer chemotherapeutic agent is a chemical compound or biological agent that retards, slows, or stops the growth of cancer or is approved to treat cancer by the U.S. Food and Drug Administration. Examples of cancer chemotherapeutic agents include, but are not limited to: paclitaxel, docetaxel, imatinib mesylate, sunitinib malate, cisplatin, etoposide, vinblastine, methotrexate, adriamycin, cyclophosphamide, doxorubicin, daunomycin, 5-fluoruracil, vincristine, endostatin, angiostatin, bevacizumab, and rituximab. Another example of a cancer treatment agent is radiation. Thus, the cancer treatment may comprise radiotherapy, fractionated radiotherapy, chemotherapy, or chemo-radiotherapy (a combination of one or more chemotherapeutic agents and radiation). "Biological" anti-cancer agents include e.g. antibodies, proteins, RNA, siRNA, single guide RNA (sgRNA), DNA, etc.

As defined herein, an "aggressive cancer treatment" or "aggressive cancer treatment regimen" is generally determined by a medical professional such as a physician and/or radiologist and can be specific for each patient. In some aspects, an aggressive cancer treatment regimen is as defined by the National Comprehensive Cancer Network (NCCN), and has been defined in the NCCN Guidelines™ as including one or more of 1) intensified imaging (CT scan, PET/CT, MRI, chest X-ray), 2) discussion and/or offering of sentinel lymph node biopsy with subsequent partial or complete lymphadenectomy, 3) inclusion in ongoing clinical trials, and 4) therapeutic intervention with interferon alpha treatment and radiation to nodal basin. In general, the phrase "aggressive cancer treatment" refers to a cancer treatment, or combination of treatments, and/or a chemotherapy regimen that is effective for treating the target cancer tumor or cell, but is associated with or known to cause higher toxicity and more side effects than another type of treatment for the specified cancer type. Aggressive treatment may include one or more of surgical intervention, chemotherapy, radiation therapy, adjuvant therapy, hormone therapy, close clinical surveillance, etc. Aggressive treatment may comprise proactive treatment to reduce or prevent metastasis, including distant or multiple metastases, e.g. using systemic chemotherapy. For aggressive treatment, exceptionally toxic chemotherapeutic agents may be preferred, as may higher and/or more frequent doses of one or more anti-cancer agents, and/or a longer course duration of therapy (chemotherapy, radiation, etc.), and/or a repetition of therapy. For example, a radical mastectomy may be recommended, together with lymph node removal, chemotherapy and radiation for a breast cancer patient.

Less aggressive treatment may also comprise surgical intervention, chemotherapy, radiation therapy, adjuvant therapy, hormone therapy, or close clinical surveillance, etc. It may also comprise proactive treatment to reduce or prevent local, organ-specific, tissue specific, or site-specific metastasis. However, in general, the treatment may be more localized and focus on the primary tumor, using e.g. resection followed by targeted drug therapy, such as treatment using antibodies which target the particular tumor type, or an implanted radiation source, etc. For breast cancer, a lumpectomy may be recommended to remove a cancerous breast tumor, preceded by neo-adjuvant treatment to shrink the tumor prior to surgery, rather than a radical mastectomy. If a course of radiation is prescribed, it may be a shorter and/or less intense course than that which is recommended for aggressive treatment.

In general, one of skill in the art will be able to determine if a cancer treatment, combination of treatments, or chemotherapy regimen is less or more, and this may vary by cancer type, the age and general physical health of the patient, etc. For example, a less aggressive treatment may include adjuvant chemotherapy comprising surgical resection of the primary tumor and a chemotherapy regimen comprising 5-FU, leucovorin and bevacizumab, while a more aggressive cancer treatment may include adjuvant chemotherapy comprising surgical resection and a chemotherapy regimen comprising FOLFOX and BV, and the most aggressive cancer treatment may include surgical resection and a chemotherapy regime comprising Irinotecan and Cetuximab.

In addition, some subjects who have not been diagnosed with cancer but who are at high risk of developing cancer may benefit from monitoring TMEM219 expression on an ongoing basis. Examples of such subjects include but are not limited to subject with a genetic predisposition to develop cancer (e.g. women with mutations in one or both of the BRCA1 and BRCA2 genes), or who have experienced an environmental insult that may result in cancer (e.g. exposure to radiation, inhalation of toxic particles, contact with carcinogenic chemicals, etc.) or who have or are engaged in high risk activities with respect to cancer such as smoking. Such subject may be monitored on an ongoing basis by determining TMEM219 expression levels over an extended period of time (months or years) and by a comparison of early, non-symptomatic levels in a tissue of interest (e.g. breast or lung tissue) to levels measured over time, or to a relevant reference value. In this manner, the development of cancerous tissues may be detected and early treatment can begin.

Cancer Treatment

In other aspects, the present disclosure also provides IGFBP-3R agonists for use in the treatment of cancer. The patient may or may not have been diagnosed using the methods described in the preceding section. The agonists advantageously cause cancer cell death without killing normal, non-tumor cells. Generally, the IGFBP-3R agonists are mAbs as disclosed herein, and the methods involve preventing or treating cancer by administering a therapeutically effective amount of at least one of agonist of the IGFBP-3R, such as a mAb disclosed herein.

In some aspects, the antibodies are used in single-agent therapy. In other aspects, the antibodies are used in combinatorial antitumor activity (which may give additive or synergistic results) with other chemotherapeutic agents including but are not limited to iniparib, gemcitabine, onartuzumab carboplatin, cisplatin, paclitaxel, bortezomib, erlotinib, everolimus, synribo, etoposide, doxorubicin, venetoclax, navitoclax, nivolumab and pembrolizumab. In addition, the agonists may be used in combination with other cancer therapies such as radiation, surgery/resection, In some aspects, the cancer that is treated is breast cancer (e.g. TNBC), colon cancer, lung cancer, ovarian cancer, pancreatic cancer, head and neck cancer, prostate cancer, liver cancer or a liquid tumor (e.g. a leukemia), etc.

For the treatment of cancer, the amount of antibody that is administered is generally in the range of from about 1-100 mg/kg, and is preferably from about 5 to 50 mg/kg, e.g. about 5, 10, 15, 20, 25, 30, 35, 40, 45 or 50 mg/kg.

Metabolic Syndrome

"Metabolic syndrome", a cluster of conditions which occur together, is known to increase the risk of heart disease, stroke and type 2 diabetes. In fact, Type 2 diabetes is sometimes considered a "complication" of metabolic syndrome, and "pre-diabetes" and metabolic syndrome are considered by some to be the same disease. Although diagnostic guidelines differ among e.g. the American Heart Association, the World Health Organization, and other institutions, metabolic syndrome is generally diagnosed in a subject when e.g. at least 3 of the following conditions are present: increased or high blood pressure, high blood sugar, excess body fat around the waist, abnormally low HDL cholesterol and high triglyceride levels.

"High blood pressure" generally refers to blood pressure of 140 systolic or higher and/or 90 diastolic or higher that stays high over time. In some aspects, blood pressure of 130/85 or more is taken as diagnostic for metabolic syndrome, when taken together with e.g. at least 2 other relevant symptoms.

"High blood sugar" generally refers to a blood sugar that is higher than 130 mg/dL (milligrams per deciliter) after not eating or drinking for at least 8 hours, although in some aspects a fasting blood glucose level of 100 mg/dl or above is taken as diagnostic for metabolic syndrome, when taken together with other relevant symptoms. High blood sugar is generally caused by insulin resistance, and insulin resistance may be included as a hallmark of metabolic disease.

Central obesity (also known as abdominal, visceral, male-pattern or apple-shaped adiposity) and/or the presence of ectopic fat are diagnostic criteria for metabolic syndrome. Central obesity generally refers to a large waist circumference e.g. for a man, a waist circumference of at least 40 inches (102 centimeters) and for a woman at least 35 inches (89 centimeters). For ethnic Asian Americans, the cutoff values are ≥90 cm (35 in) in men or ≥80 cm (32 in) in women. Ectopic fat refers to fat deposition in organs/tissues that do not normally store fat.

A fasting HDL cholesterol level of 40 mg/dl or lower in men and 50 mg/dl or lower in women (dyslipidemia) is a hallmark of metabolic disorder. This may also be referred to as abnormal (high) cholesterol, lipid disorder, dyslipidemia, hyperlipidemia, or hypercholesterolemia, etc. Some practitioners use total (HDL and LDL) cholesterol levels, which are considered high at levels of more than 200 mg/dL, e.g. 200 to 239 mg/dL may be referred to as "borderline high," and 240 mg/dL or more may be considered "high".

"High triglyceride levels" (dyslipidemia) generally refers to triglyceride levels that are at least higher than 100 milligrams per deciliter of blood (mg/dL), with borderline high levels being 150 to 199 mg/dL, high levels being 200 to 499 mg/dL and very high levels being 500 mg/dL and above. According to some guidelines, serum triglycerides of 150 mg/dl or above are considered diagnostic, when taken together with at least 2 other relevant symptoms.

Based on the guidelines from the National Heart, Lung, and Blood Institute (NHLBI) and the American Heart Association (AHA), any three of the preceding traits in the same individual meet the criteria for a diagnosis of metabolic syndrome. In addition, it is noted that insulin resistance, metabolic syndrome, and prediabetes are closely related to one another and have overlapping aspects, and each of these may be treated or prevented by the practice of the methods described herein.

In particular, insulin resistance is a syndrome (a set of signs and symptoms) that is also part of the larger constellation of symptoms called the metabolic syndrome. Insulin resistance (IR) is a pathological condition in which cells fail to respond normally to the hormone insulin. Normally, the body produces insulin when glucose starts to be released into the bloodstream from the digestion of carbohydrates in the diet, and this insulin response triggers glucose being taken into body cells, to be used for energy, and inhibits the body from using fat for energy. The concentration of glucose in the blood decreases as a result, staying within the normal range even when a large amount of carbohydrates is consumed. When the body produces insulin under conditions of insulin resistance, the cells are resistant to the insulin and are unable to use it as effectively, leading to high blood sugar. Beta cells in the pancreas subsequently increase their production of insulin, further contributing to a high blood insulin level. People who develop type 2 diabetes usually pass through earlier stages of insulin resistance and prediabetes. Insulin resistance may also develop in patients who have recently experienced abdominal or bariatric procedures, although this acute form of post-operative insulin resistance tends to be short term.

The present disclosure provides IGFBP-3R agonists for use in the prevention and treatment of metabolic syndrome, i.e. one or more of the symptoms, signs or criteria used for diagnosing metabolic syndrome is prevented or treated by administering one or more of the agonists described herein, including insulin resistance. In some aspects, the agonists are monoclonal antibodies (mAbs) specific for binding to the receptor "IGFBP-3R" as disclosed herein. Thus, the agonists are used to prevent or treat metabolic syndrome and/or complications thereof, and/or diseases caused by metabolic syndrome, e.g. to prevent symptoms from worsening and/or causing even more serious conditions such as heart disease, stroke and type 2 diabetes.

For the treatment of metabolic syndrome, the amount of antibody that is administered is generally in the range of from about 1-100 mg/kg, and is preferably from about 5 to 50 mg/kg, e.g. about 5, 10, 15, 20, 25, 30, 35, 40, 45 or 50 mg/kg.

Obstructive Respiratory Diseases

Obstructive lung disease is a category of respiratory disease characterized by airway obstruction. Many obstructive diseases of the lung result from narrowing of the smaller bronchi and larger bronchioles, often because of excessive contraction of the smooth muscle itself. It is generally characterized by inflamed and easily collapsible airways, obstruction to airflow, problems exhaling and frequent medical clinic visits and hospitalizations. Types of obstructive lung disease include; asthma, bronchiectasis, bronchitis and chronic obstructive pulmonary disease (COPD). Although COPD shares similar characteristics with all other obstructive lung diseases, such as the signs of coughing and wheezing, they are distinct conditions in terms of disease onset, frequency of symptoms and reversibility of airway obstruction. Cystic fibrosis is also sometimes included in obstructive pulmonary disease.

Obstructive respiratory disorders include but are not limited to:

Asthma (including exercise-induced asthma, occupational asthma and nocturnal asthma. Asthma is characterized by hyperresponsive bronchial tubes (airways) that become inflamed and produce excess mucus. The muscles around the airways tighten making the airways narrower. Asthma is usually triggered by e.g. dust or pollen that produces an allergic reaction, but may also be triggered by an upper respiratory tract infection, cold air, exercise or smoke. Asthma causes recurring episodes of wheezing, breathlessness, chest tightness, and coughing. Bronchiectasis, which refers to the abnormal, irreversible dilatation of the bronchi caused by destructive and inflammatory changes in the airway walls. Bronchiectasis has three major anatomical patterns: cylindrical bronchiectasis, varicose bronchiectasis and cystic bronchiectasis.

Chronic obstructive pulmonary disease, a term that includes the conditions emphysema and chronic bronchitis. Most patients with COPD have characteristics of both conditions to varying degrees and typically the symptoms are irreversible. However, many COPD patients have some degree of reversibility in their airways.

The subjects who are treated using the methods described herein have generally been diagnosed with one or more obstructive respiratory diseases. Identifying such subjects depends on several factors and on the exact disease being diagnosed. However, one commonality among patients is an FEV1/FVC ratio of less than 0.7, i.e. the inability to exhale 70% of their breath within one second.

For the treatment of an obstructive respiratory disease, the amount of antibody that is administered is generally in the range of from about 1-100 mg/kg, and is preferably from about 5 to 50 mg/kg, e.g. about 5, 10, 15, 20, 25, 30, 35, 40, 45 or 50 mg/kg.

Inflammatory Disorders

In other aspects, the compositions and method described herein are used to prevent or treat inflammatory disorders. Inflammatory disorders generally result when the immune system attacks the body's own cells or tissues (auto-inflammatory diseases), causing chronic abnormal inflammation and resulting in chronic pain, redness, swelling, stiffness, and damage to normal tissues.

Exemplary inflammatory disorders that may be prevented/treated include but are not limited to: ulcerative colitis, colitis, Crohn's disease, atherosclerosis, chronic peptic ulcer, chronic obstructive lung disease, idiopathic pulmonary fibrosis, tuberculosis, arthritis (osteoarthritis, rheumatoid arthritis (RA), psoriatic arthritis), chronic sinusitis, asthma, hepatitis, ankylosing spondylitis, liver fibrosis, non-alcoholic steatohepatisis and chronic periodontitis.

For the treatment of inflammation and/or an inflammatory disorder, the amount of antibody that is administered is generally in the range of from about 1-100 mg/kg, and is preferably from about 5 to 50 mg/kg, e.g. about 5, 10, 15, 20, 25, 30, 35, 40, 45 or 50 mg/kg.

Examples

Figure 1B:
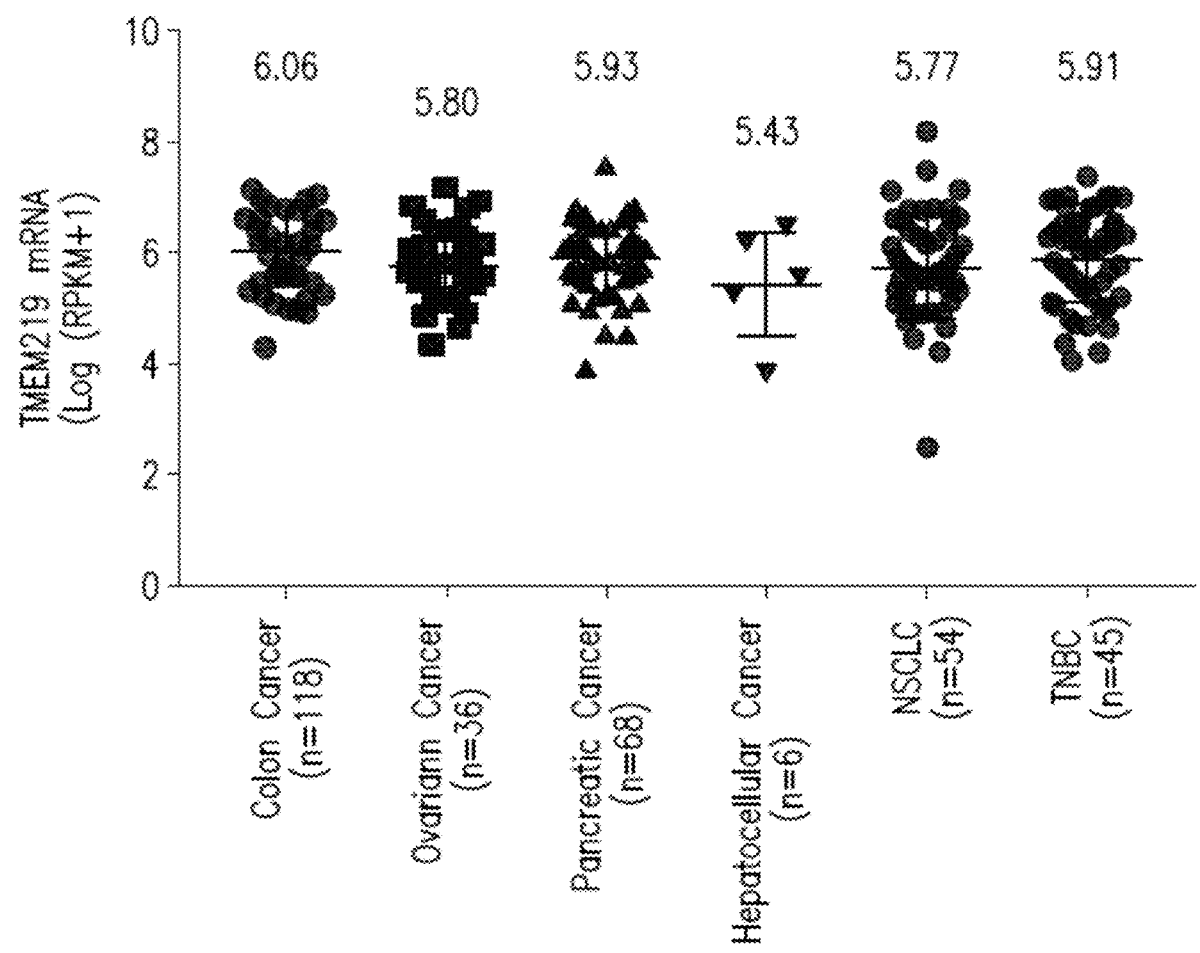

Example 1. Diagnostics: TMEM219 as a Molecular Marker for Predicting Recurrence and Survival in Cancer Bioinfoaatics analysis ofThe Cancer Genome Atlas (TCGA) data showed that AGFBP-3 is significantly lower in breast cancer, whereas expression ofTMEM219 is similar or higher in breast, colon and lung cancers compared to normal tissues. This finding shows that the antitumor IGFBP-3/TMEM219 axis is impaired during tumorigensis progression of cancer due to suppressed expression ofGFBP-3 but not its receptor TMEM219 (FIG. 1). Further assessment using data from the METABRIC study (Curtis et al., Nature. 2012:486 (7403):346-52) and the SynTarget tool [Pub Med PMID: 26915292] showed that TMEM219 expression is strongly correlated with survival of breast cancer (Table 1).

TABLE 1

Assessment of Correlation of TMEM219 with Survival of Breast Cancer Patients using the SynTarget tool

| Cancer Subtype (Clinical Variable) | Gene ID (Probe ID) | Survival Effect | p-value |
|---|---|---|---|
| All samples | TMEM219 (ILMN_1737644) | Pos | 5.32e−07 |
| Histological_type = "IDC" | TMEM219 (ILMN_1737644) | Pos | 1.58e−06 |
| HER2_SNP6_state = "NEUT" | TMEM219 (ILMN_1737644) | Pos | 3.95e−06 |
| Menopausal_status_inferred = "post" | TMEM219 (ILMN_1737644) | Pos | 4.38e−05 |
| Her2.Expr = "-" | TMEM219 (ILMN_1737644) | Pos | 7.31e−05 |
| HER_IHC_status = "null" | TMEM219 (ILMN_1737644) | Pos | 0.000146 |
| ER.Expr = "+" | TMEM219 (ILMN_1737644) | Pos | 0.000569 |
| PR.Expr = "+" | TMEM219 (ILMN_1737644) | Pos | 0.000652 |
| HER2_IHC_status = "1" | TMEM219 (ILMN_1737644) | Pos | 0.000655 |
| ER_IHC_status = "pos" | TMEM219 (ILMN_1737644) | Pos | 0.000817 |
| Site "2" | TMEM219 (ILMN_1737644) | Pos | 0.00102 |
| Celluarlity = "high" | TMEM219 (ILMN_1737644) | Pos | 0.00107 |
| Menopausal_status_inferred = "pre" | TMEM219 (ILMN_1737644) | Pos | 0.00121 |
| Stage = "null" | TMEM219 (ILMN_1737644) | Pos | 0.00123 |
| Grade = "3" | TMEM219 (ILMN_1737644) | Pos | 0.00144 |
| Stage = "2" | TMEM219 (ILMN_1737644) | Pos | 0.00174 |
| Cellularity = "moderate" | TMEM219 (ILMN_1737644) | Pos | 0.00257 |
| Lymph_nodes_positive = "2" | TMEM219 (ILMN_1737644) | Pos | 0.00559 |
| Grade = "2" | TMEM219 (ILMN_1737644) | Pos | 0.00608 |
| P53_mutation_status = "WT" | TMEM219 (ILMN_1737644) | Pos | 0.00809 |

Figure 2:
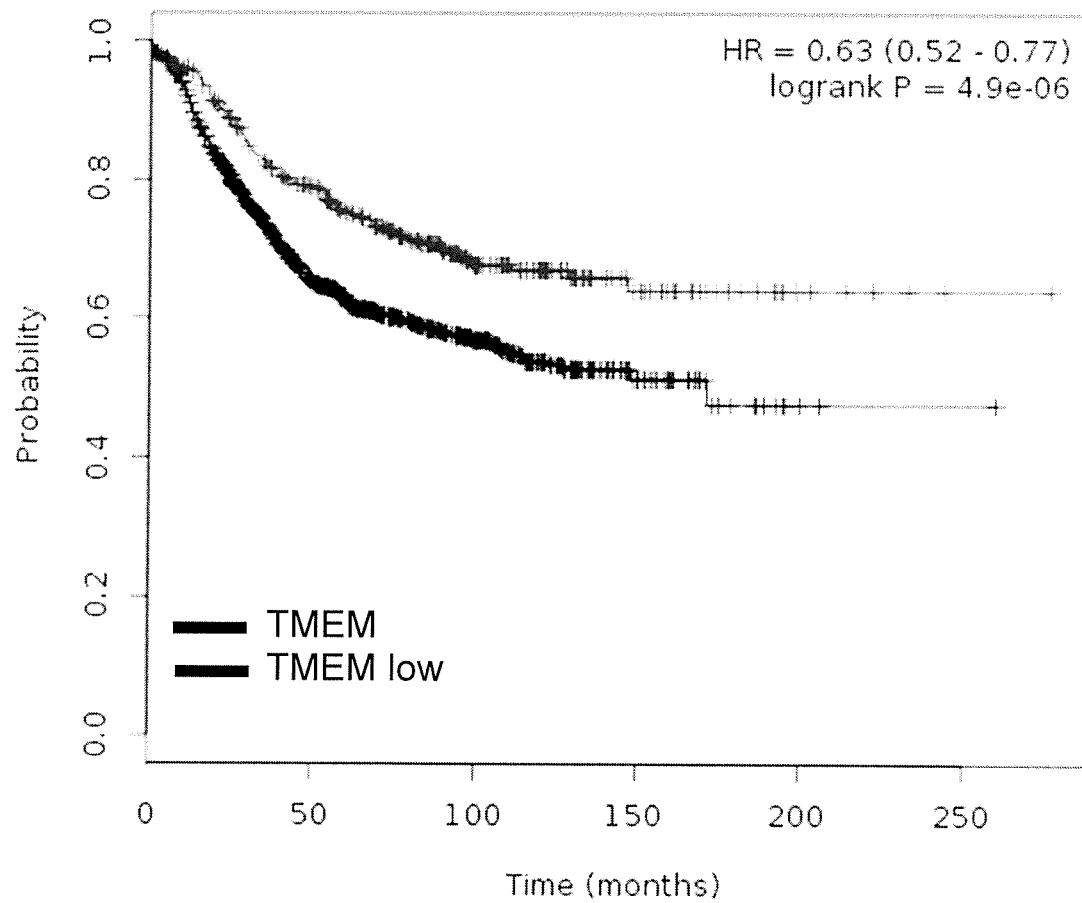
FIG. 2. The effect of high/low expression of TMEM219 on survival of breast cancer patients. Assessment of KM plot analysis shows significant survival difference between groups of breast cancer patients having high (n=423) and low (n=1237) TMEM219 expression (p-value=4.9E-6, HR=0.63, CI 0.52-0.77).
Figure 3A:
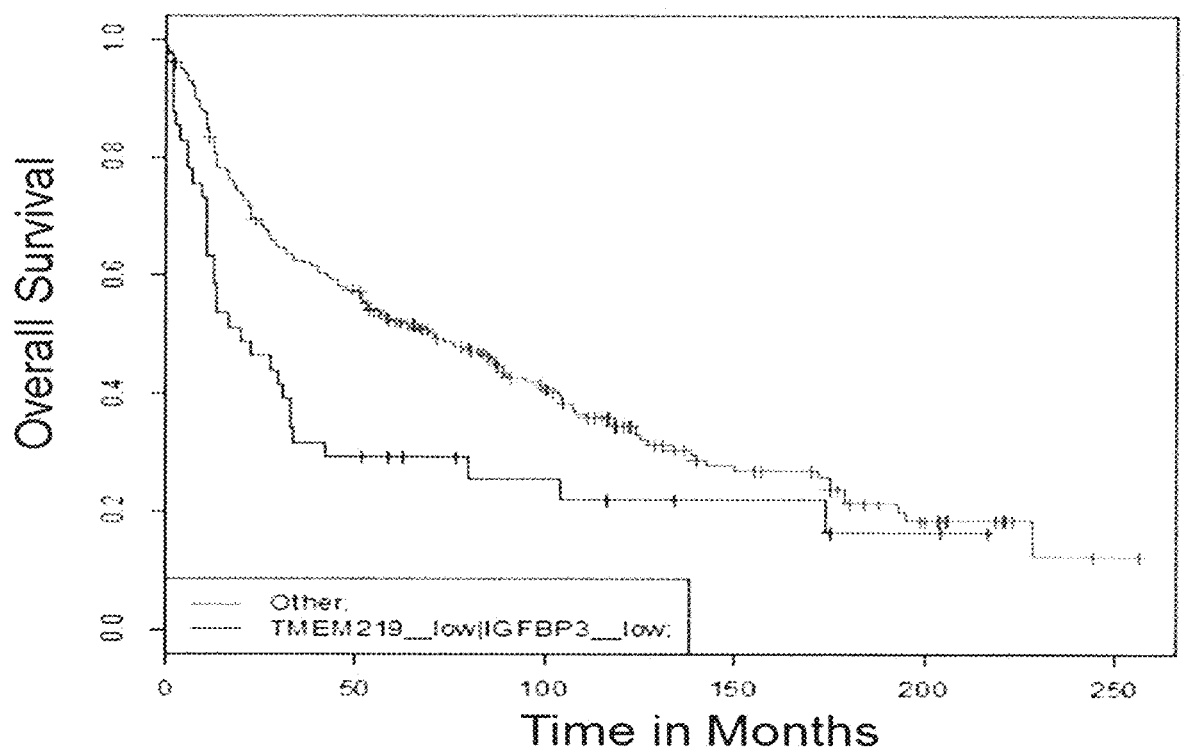
FIG. 3A-D. Impact of IGFBP-3/IGFBP-3R expression on survival in lung cancer patients. The effect of high/low expression of TMEM219 on survival of lung cancer patients was assessed using the SynTarget tool and the data from the GSE30219 study.TMEM219 expression was ranked into high (n=162) vs. low (n=131) groups based on median expression. The log rank p-value (p-value=0.00108) was assessed. A, TMEM219: low, IGFBP3: low; B, TMEM219: high, IGFBP3: high; C, TMEM219: high, TMEM219: low; D, IGFBP3: high, IGFBP3: low.
Figure 3B:
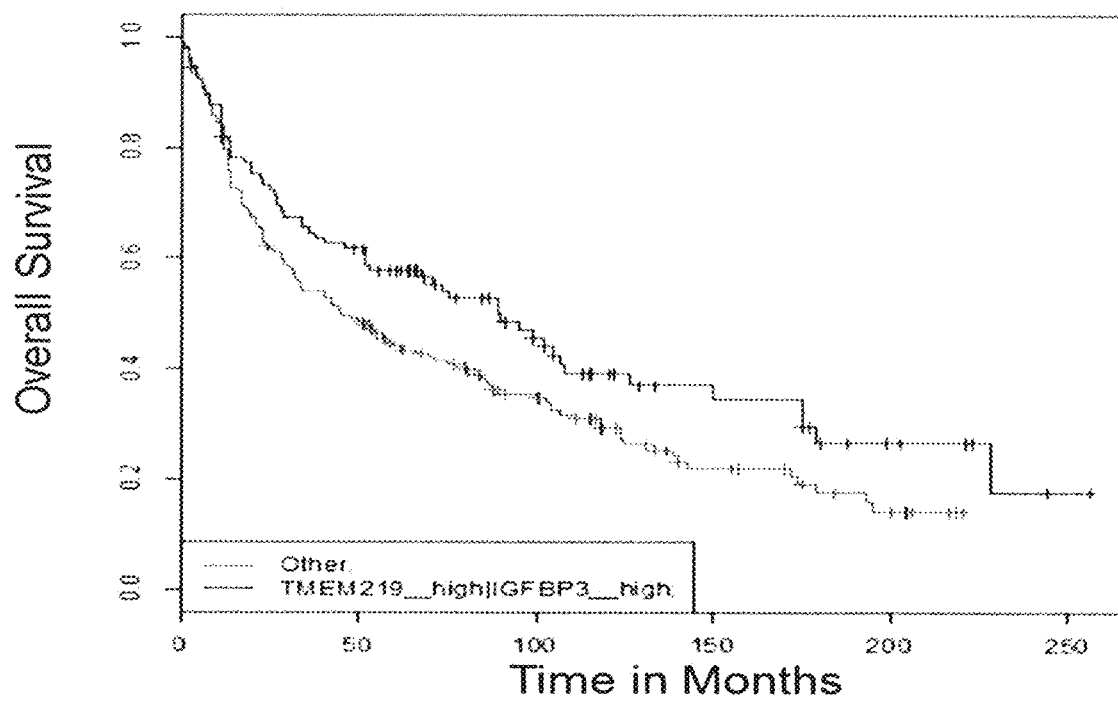
Figure 3C:
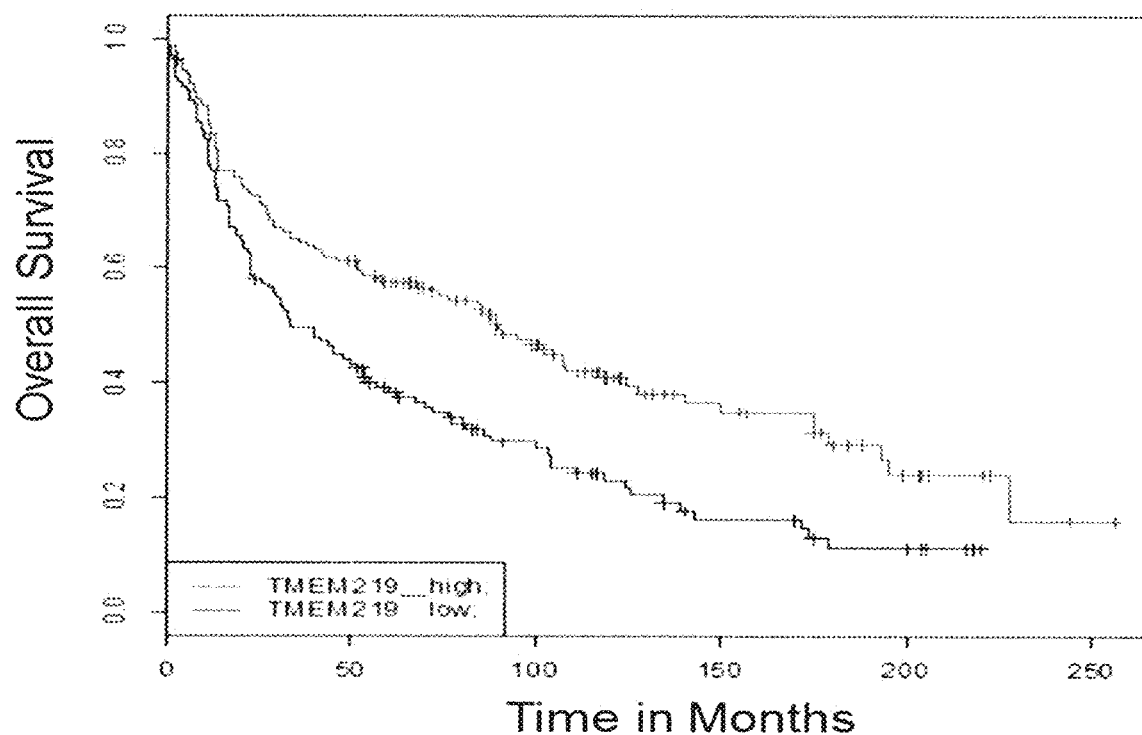
Figure 3D:
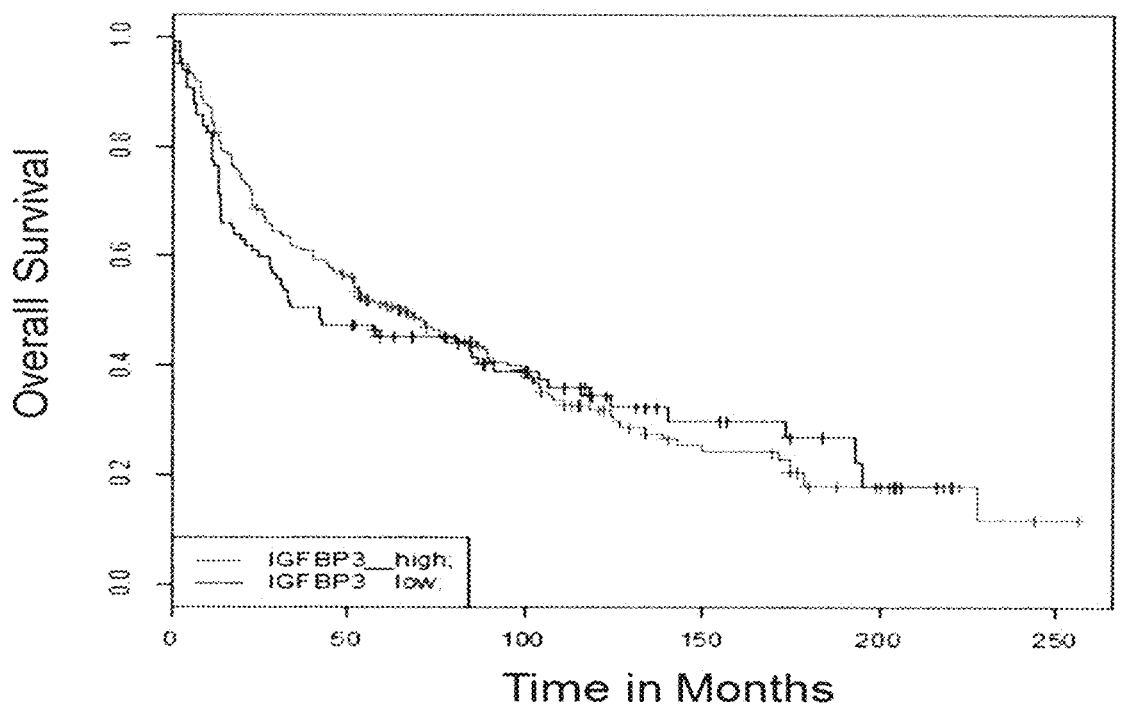

These results were confirmed using the Kaplan-Meyer survival analysis, which detected a significant survival difference between groups of patients having high (n=423) and low (n=1237) TMEM219 expression [p-value=4.9E-6, hazard ratio (HR)=0.63, confidence interval (CI) 0.52-0.77)] (FIG. 2). This strong correlation is also observed in colon and lung cancer (Table 2, FIG. 3).

TABLE 2

Assessment for Correlation of TMEM219 with Survival of Colon and Lung Cancer Patient using SynTarget Tool

| GEO Dataset ID | Cancer Type | Cancer Subtype (Clinical Variable) | Gene IS (Probe ID) | Survival Effect | p-value |
|---|---|---|---|---|---|
| GSE30219 | Lung | all samples | TMEM219(224981_AT) | positive | 0.0010 |
| GSE30219 | Lung | gender = F | TMEM219(224981_AT) | positive | 0.0074 |
| GSE39582 | Colon | tnm.stage = 1 | TMEM219(228513_AT) | positive | 0.0094 |
| GSE39582 | Colon | cit.molecular subtype = C5 | TMEM219(228513_AT) | positive | 0.018 |

TABLE 2-continued

Assessment for Correlation of TMEM219 with Survival of Colon and Lung Cancer Patient using SynTarget Tool

| GEO Dataset ID | Cancer Type | Cancer Subtype (Clinical Variable) | Gene IS (Probe ID) | Survival Effect | p-value |
|---|---|---|---|---|---|
| GSE39582 | Colon | tumor.location = distal | TMEM219(228513_AT) | positive | 0.021 |
| GSE39582 | Colon | mmr.status = pMMR | TMEM219(228513_AT) | positive | 0.025 |

These findings provide solid evidence for TMEM219 as a molecular marker for predicting recurrence and survival in breast, colon and lung cancer. Oncotype DX, a very expensive gene test, is routinely used in hospitals to predict chemotherapy benefit and recurrence risk of patients with breast, colon and prostate cancer. The present TMEM219 assay is an excellent tool for replacing or complementing the Oncotype DX test.

Figure 4:
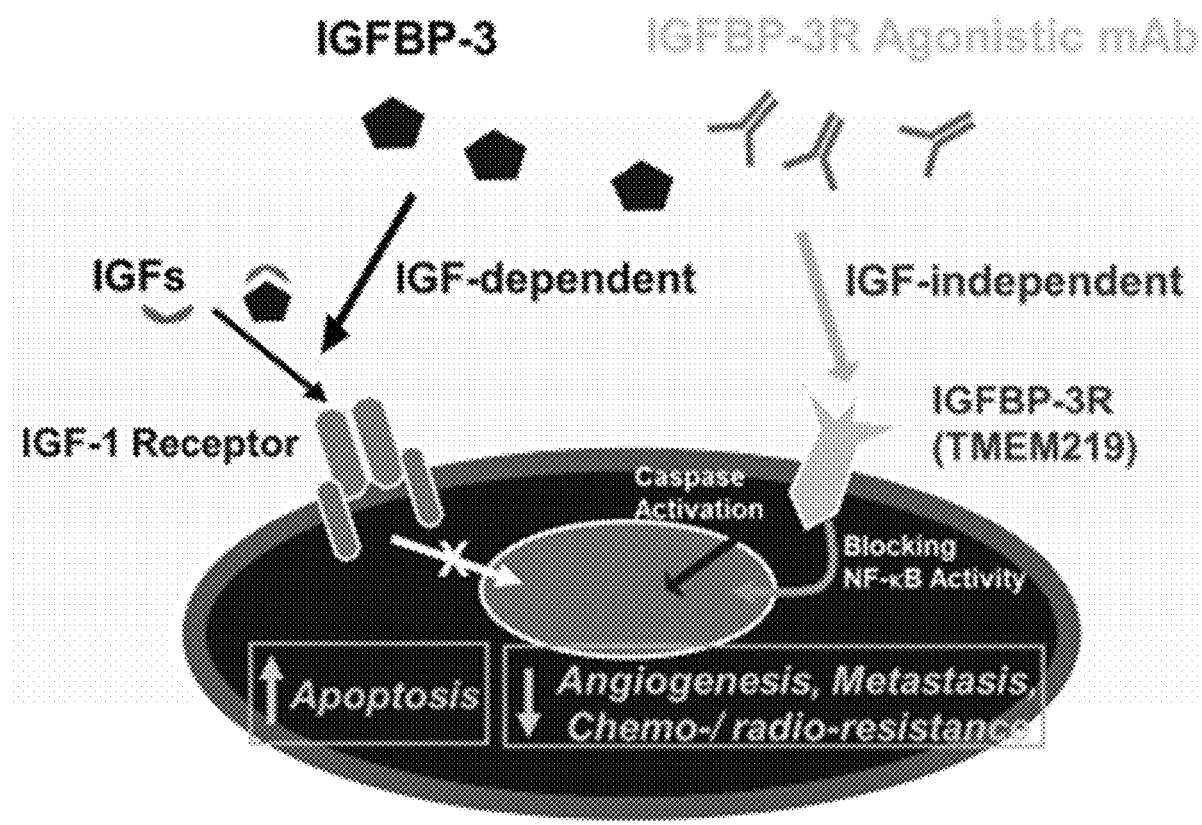
FIG. 4. Schematic representation of the TMEM219/IGFBP-3 interaction in the cell, a central pathway for IGFBP-3-induced inhibition of tumor growth, tumor angiogenesis, metastasis and chemo-resistance via induction of apoptosis and suppression of tumor-induced NF B activity in cancer cells.

FIG. 4 depicts a schematic overview of the mechanism of action of the IGFBP-3/TMEM219 axis in cancer.

Example 2. Agonist Antibodies and Cancer

The naturally occurring TMEM219 agonist does not in and of itself represent a useful therapeutic agent due to significant post-translational modification: proteolysis induced by tumor activated proteases attenuates TMEM219 antitumor signaling. Thus, monoclonal antibodies (mAbs) that activate TMEM219, i.e. "agonist antibodies" were created. The process of manufacturing mAbs has been standardized in the art and mAbs are known to exhibit robust stability within the body, without inducing major deleterious side effects. The "agonist mAb" approach advantageously precludes the need to use toxic compounds to kill the cancer cells.

Figure 5A:
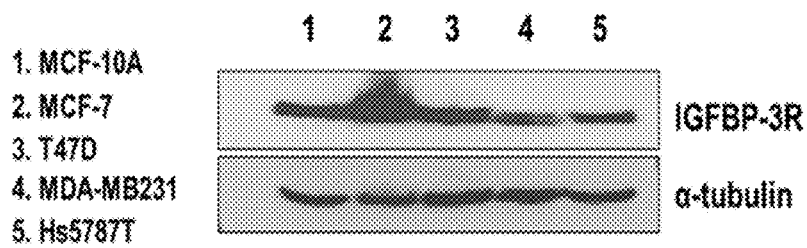
FIG. 5A-C. Growth Inhibitory Effects of TMEM219 Agonist mAbs in Breast Cancer Cells. A, A representative western immunoblot (WIB) showing TMEM219 expression in breast cancer cells. B, Breast cells were grown up to 40% confluency and treated with 30 nM IGFBP-3R agonist mAb #2 (#274) in 1% FBS containing media for 3 days. C, Similarly breast cancer cells were treated with different concentrations of TMEM219 agonist mAb #2 (#274) for 3 days and live cells were counted using the TC20 automated cell counter. n=3 in duplicate. MCF-10A: normal mammary epithelial cells; MCF-7, T47D: estrogen responsive breast cancer cells MDA-MB231, Hs578T: triple-negative breast cancer cells.
Figure 5B:
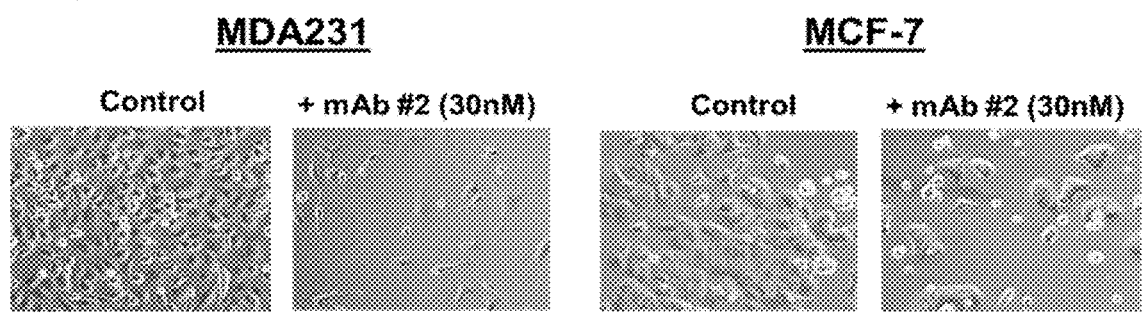
Figure 5B:
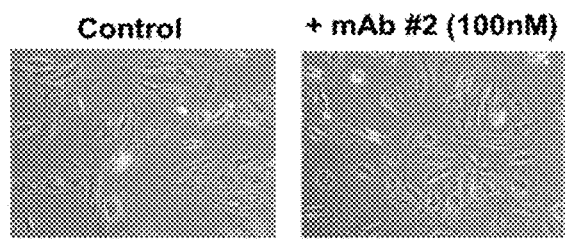
Figure 5C:
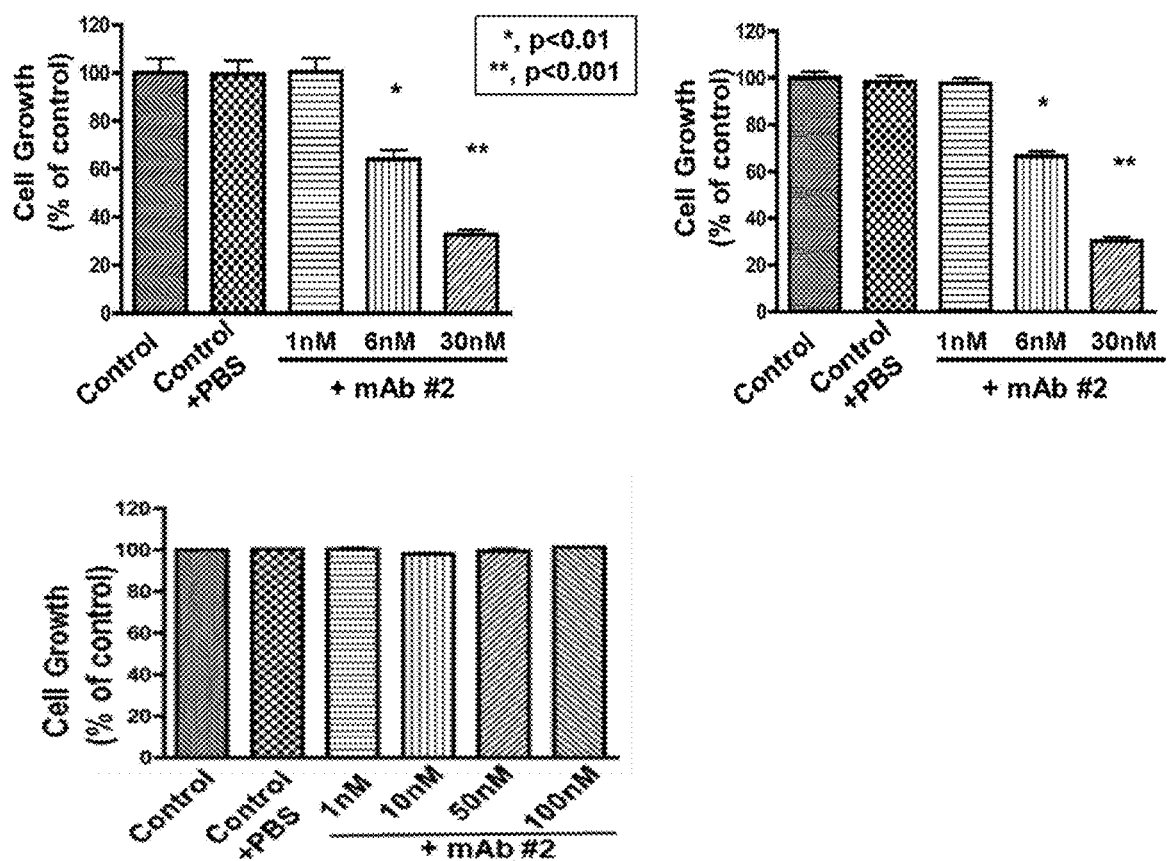

A panel of TMEM219 specific monoclonal antibodies was generated and two exemplary antibodies were sequenced (#245 and #274). Further, a TMEM219 #274-human IgG1 chimera which acts like the TMEM219 natural agonist was also developed. As shown in FIG. 5A-C, treatment with one of the hybridoma cell-produced TMEM219 agonist mAbs [TMEM219 mAb #2 (#274)] significantly inhibited not only MCF-7 estrogen-responsive breast cancer cell growth but also MDA-MB231 TNBC cell growth. However, MCF-10A normal immortalized mammary epithelial cell growth was not inhibited despite expressing a similar level of TMEM219 at the mRNA and protein levels. It was further observed that TMEM219 mAb #2 (#274) inhibits the growth of both breast cancer cell lines in a dose dependent manner with 70% growth inhibition at the concentration of 30 nM ($p<0.001$).

As described below, TMEM219 agonist mAbs have tumor suppressive activity not only on cancer cells in culture, but also in animal models of human cancer (models representing non-small cell lung cancer, triple-negative breast cancer (TNBC), colon cancer, and prostate cancer). In addition, TMEM219 agonist mAbs also suppress the tumor-activated signaling critical to tumor angiogenesis, metastasis and radio-/chemo-resistance. Of high importance is the fact that, despite strong anti-cancer cell activity, the TMEM219 agonist antibodies have no deleterious cell killing effect on normal, non-tumor cells.

Breast Cancer

Figure 6A:
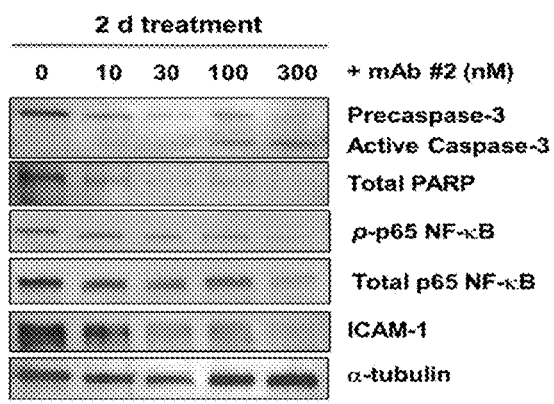
FIG. 6A-F. A, Anticancer effects of TMEM219 agonist mAb in bioluminescent MDA-MB-231 cells expressing TMEM219 but not in TMEM219-knockdown MDA231 cells. Treatment of TMEM219 mAb #2 (#274) results in significant activation of caspase-3, decrease of total PARP and suppression of tumor-activated NF-kB signaling (A), and cell growth inhibition (B). C, TMEM219 #274-hIgG1 chimera detects TMEM219 in MCF-7 cell lysates and also D, activates caspase-3 and inhibits tumor-activated NF-kB signaling in bioluminescent MDA-MB-231 cells. E, CRISPR-CAS9-mediated knockdown of TMEM219 results in complete knockdown of TMEM219 protein expression (upper panel, sgRNA-1 & sgRNA-2) and following no significant TMEM219 agonist mAb #274-induced growth inhibition (bottom panel, sgRNA-1 & sgRNA-2). F, Mechanism of Action of TMEM219 mAbs. TMEM219 agonist mAbs specifically bind to TMEM219 and exert antitumor function in human cancers via induction of caspase-dependent apoptosis and suppression of tumor-activated NF-kB signaling pathways.
Figure 6B:
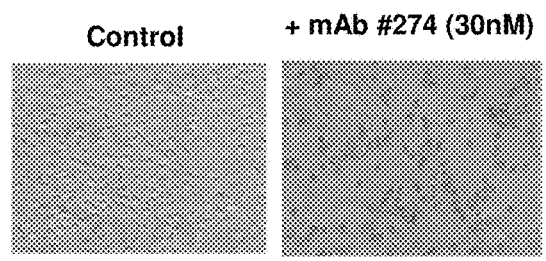
Figure 6C:
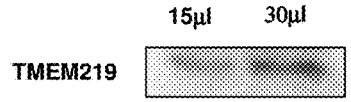
Figure 6D:
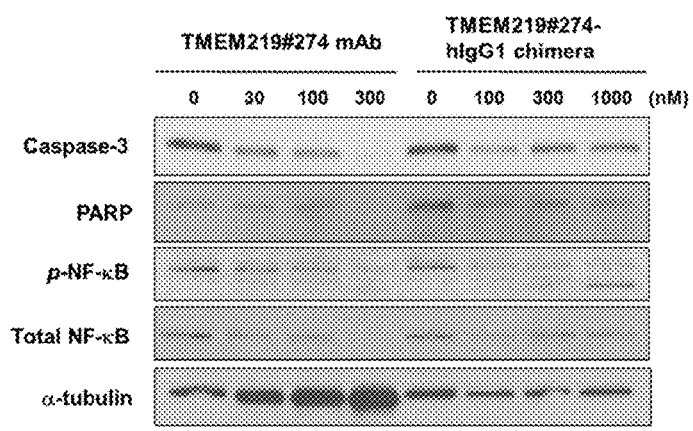
Figure 6E:
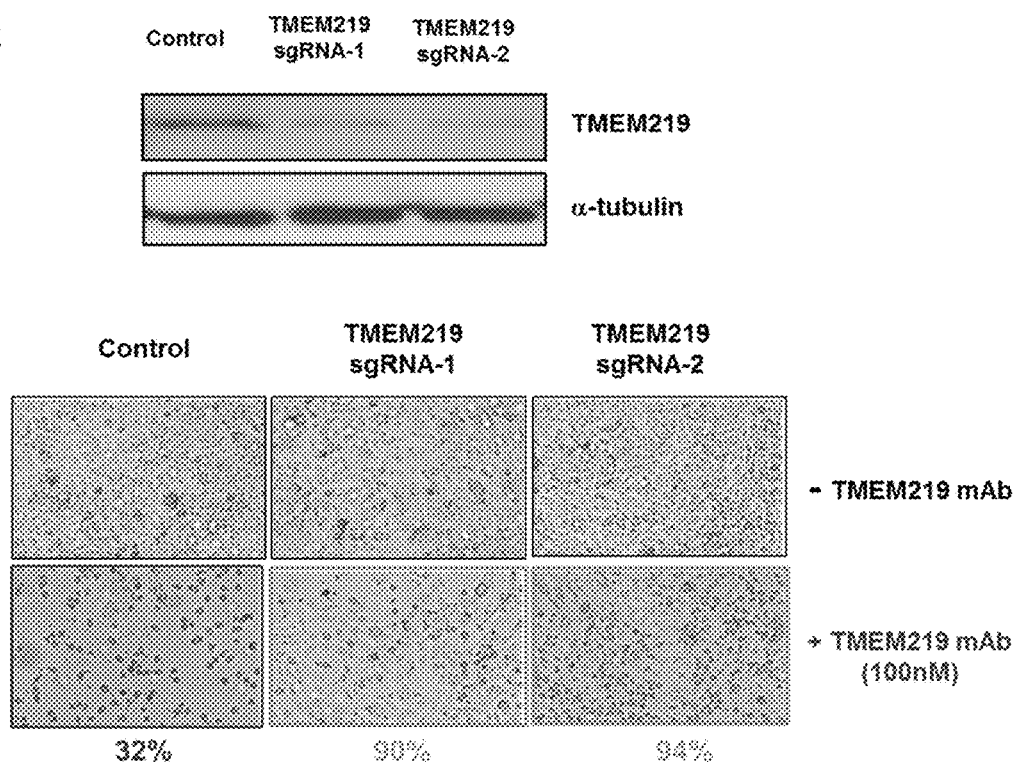
Figure 6F:
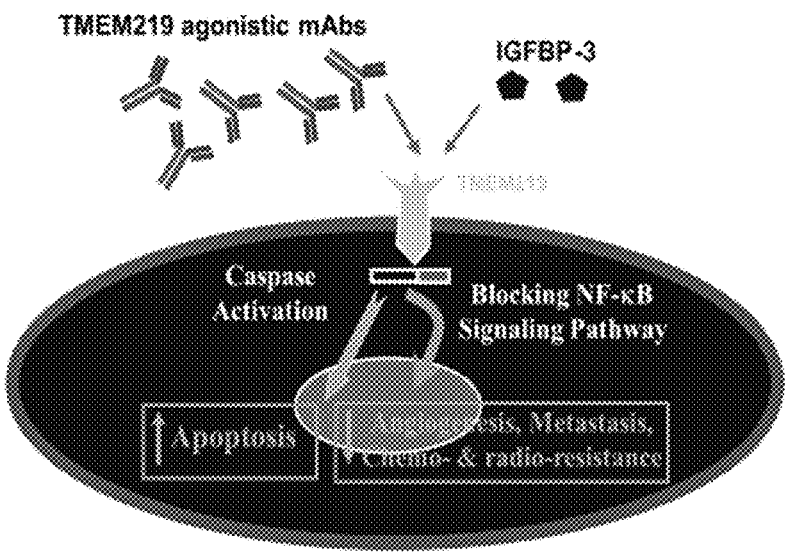

The antitumor and anti-metastatic effects of TMEM219 agonist mAbs was investigated using a bioluminescent orthotopic MDA-MB231 triple negative breast cancer (TNBC) mouse model. In vitro data using MDA-MB231 cells expressing dtTomato-Luciferase clearly demonstrates that treatment of TMEM219 agonist mAb #2 (#274) resulted in induction of caspase-dependent apoptosis as shown significant activation of caspase-3 and subsequent decrease of total PARP, and suppression of tumor-activated NF-kappa B signaling, as shown by the decrease of phospho- and total p65 NF-kappa B (FIG. 6A). Treatment of 30 nM agonist mAb #2 (#274) for 4 days resulted in significant cell death in bioluminescent MDA-MB231 cells (FIG. 6B). As similarly observed with TMEM219 #274 mAb, TMEM219 #274-hIgG1 chimera detects TMEM219 in MCF-7 cell lysates (FIG. 6C, left panel) and also activates caspase-3 and inhibits tumor-activated NF-kappaB signaling in bioluminescent MDA-MB-231 cells (FIG. 6C, right panel). Furthermore, TMEM219 knockdown using CRISPR/Cas9 gene editing techniques resulted in complete abolishment of TMEM219 agonist mAb-induced cell growth inhibition (FIG. 6D). When two different sequence targeted single guide RNA (sgRNA) constructs were transfected into bioluminescent MDA-MB231 cells, TMEM219 expression was suppressed up to 95% by each individual construct (upper panel sgRNA-1 and sgRNA-2). Treatment with 100 nM TMEM219 agonist mAbs resulted in significant growth inhibition in the control (68% inhibition), whereas only 10% and 6% growth inhibition was observed in sgRNA-1 and sgRNA-2-transfected cells, respectively, after TMEM219 agonist mAbs treatment (bottom panel). These data demonstrate that TMEM219 agonist mAbs-induced anticancer effects are mediated through TMEM219 antitumor signaling in human cancers (FIG. 6D).

Figure 7A:
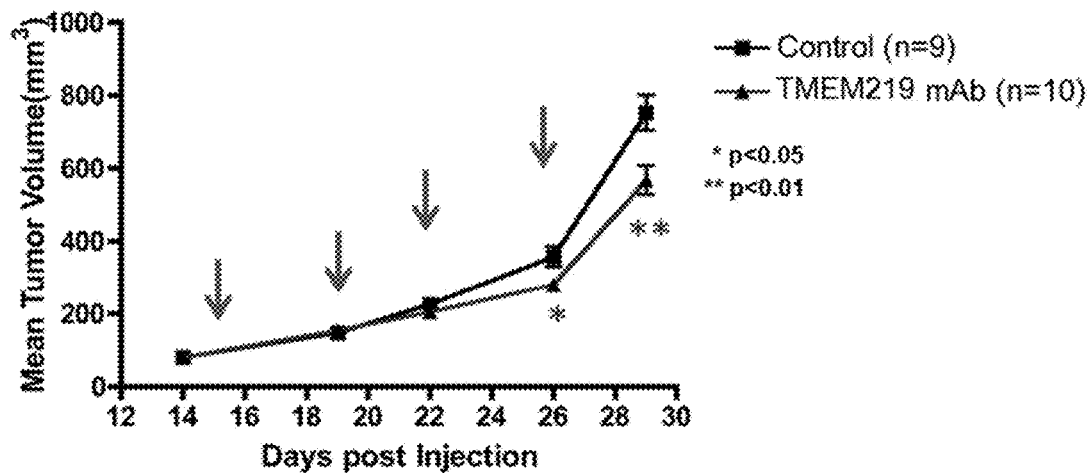
FIG. 7A-C. Antitumor Effect of TMEM219 mAb in Bioluminescent Orthotopic MDA231 TNBC Mice. TMEM219 mAb #2 (#274) administration results in tumor shrinkage up to 20% (p<0.05) and 25% (p<0.01) at day 26 and day 29, respectively after tumor cell injection (A, C). No apparent body weight and damages in major organs were observed in TMEM219 mAb administrated mice (B). TMEM219 mAb #2 (#274) was intraperitoneally administrated at the concentration of 1 mg/kg bodyweight twice per week at day 15 after tumor cell injection.
Figure 7B:
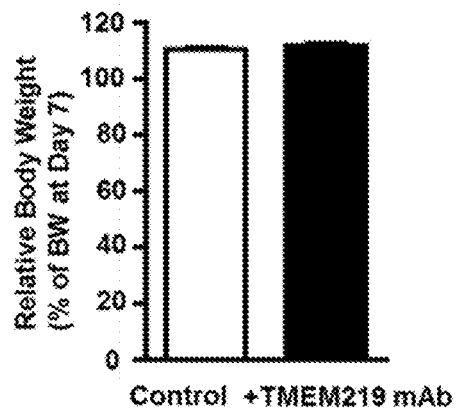
Figure 7C:
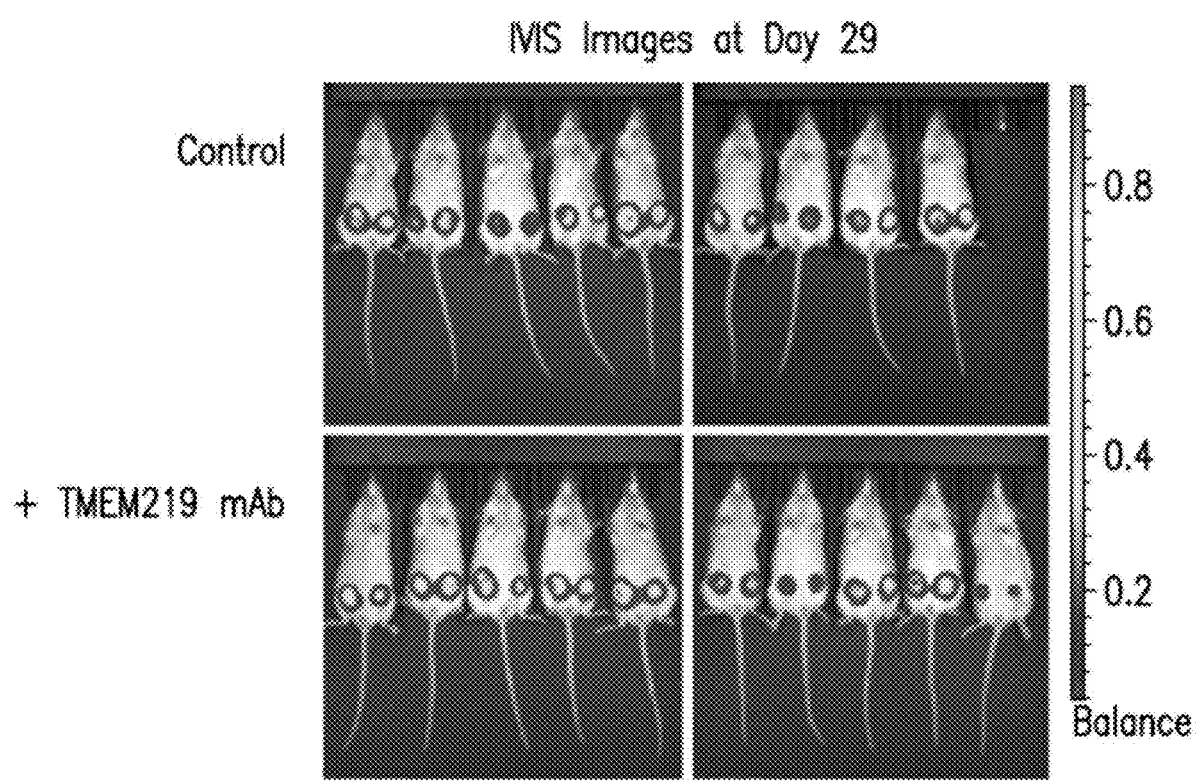

The antitumor and anti-metastatic effects of TMEM219 agonist mAbs were investigated using a bioluminescent orthotopic breast tumor mouse model. MDA-MB231 cells expressing dtTomato-Luciferase were injected into the fourth mammary fat pad of 8 week old NOD-SCID-IL27R-/- mice. As shown in FIG. 7A-C, administration of a low dose of TMEM219 mAb (1 mg/kg body weight) resulted in tumor shrinkage up to 25% ($p<0.01$) at day 29 after tumor cell injection. No detectable adverse effects, determined e.g. by body weight change and macroscopic damages in major organs such as liver, kidney and spleen, were observed.

Figure 8A:
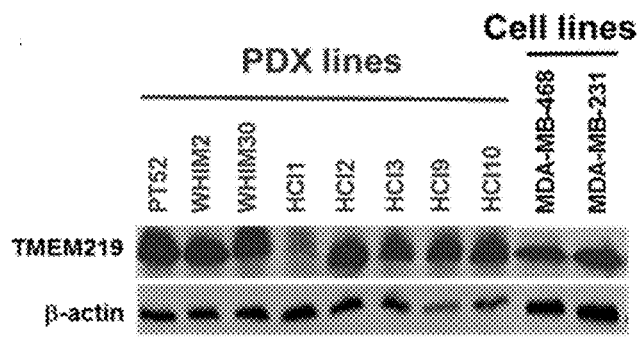
FIG. 8A-D. TMEM219 in PDX TNBC. Expression profile of TMEM219 in PDX TNBC cells at protein (A) and mRNA levels (B). Immunohistochemical staining of TMEM219 expression in chemodrug-sensitive (WHIM30) and chemodrug-resistant (WHIM2) cells (C). Original magnification, x40. Growth inhibitory effect of TMEM219 Agonist mAbs in chemodrug-sensitive and chemodrug-resistant PDX TNBC Cells (D). Cells were treated with mAb #2 (#274) for 3 days. n=3, p/s: Radiance Photons/Second. ***, p<0.001, vs Vehicle (mouse IgG 50 nM).
Figure 8B:
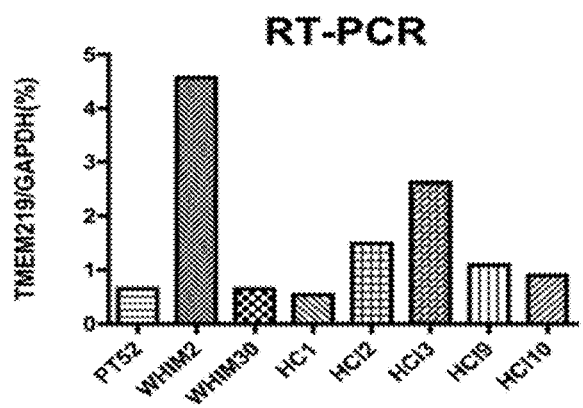
Figure 8C:
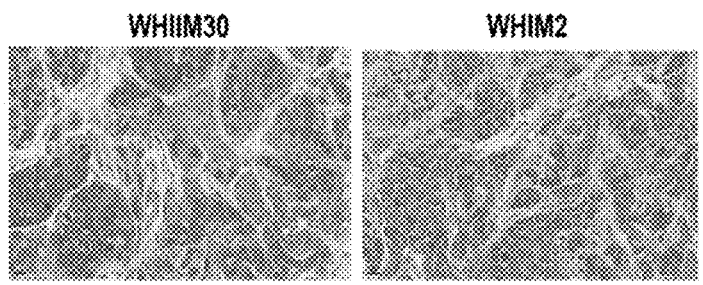
Figure 8D:
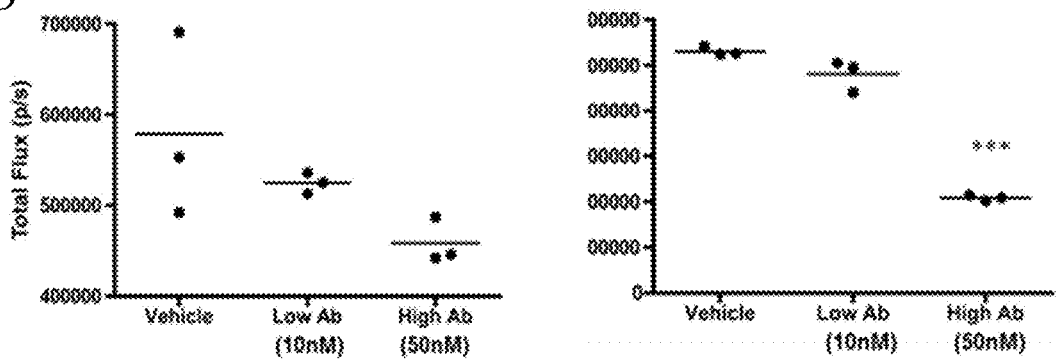

The expression profiles of TMEM219 and the antitumor effect of TMEM219 agonist mAb were examined in Patient Derived Xenograft (PDX) TNBC cells. As shown in FIG. 8, TMEM219 is readily detectable in all TNBC PDX cells tested at the protein and mRNA levels (FIGS. 8A and 8B). Those expression levels were comparable to the established TNBC cells, MDA-MB231 and MDA-MB468. In addition, immunohistochemistry data clearly demonstrate that TMEM219 is expressed in both PDX tumors and present mainly in cell membrane and cytoplasmic region but not in the nucleus (FIG. 8C). Furthermore, TMEM219 agonist mAb #2 (#274) treatment resulted in a significant growth inhibition not only in chemodrug-sensitive WHIM30 but also in chemodrug-resistant WHIM2 PDX TNBC cells (FIG. 8D).

Figure 9A:
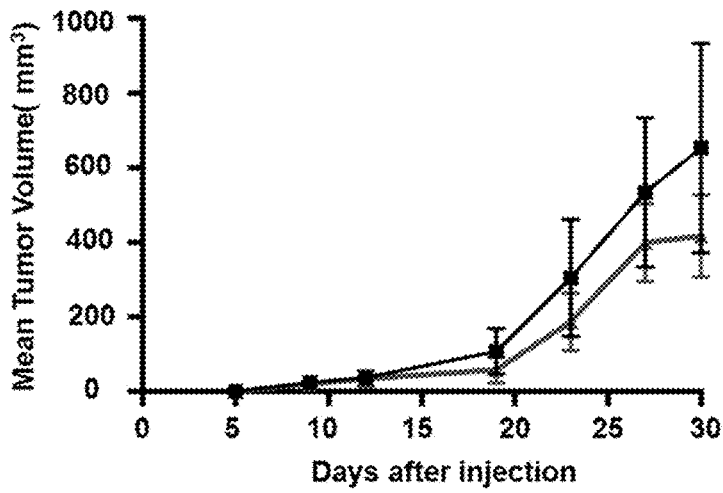
FIG. 9A-D. Antitumor Effect of TMEM219 mAb in Bioluminescent Orthotopic WHIM30 PDX TNBC Mice. TMEM219 mAb #2 administration results in tumor shrinkage up to 29% at day 30 after tumor cell injection (A). No apparent body weight and damages in major organs were observed in TMEM219 mAb administrated mice (B). Comparison of primary tumor size (C) weight (D) between mouse IgG treated control and TMEM219 mAb administrated tumors at day 30. Mouse IgG or TMEM219 mAb #2 was intraperitoneally administrated at the concentration of 1 mg/kg bodyweight twice per week at day 5 after tumor cell injection.
Figure 9B:
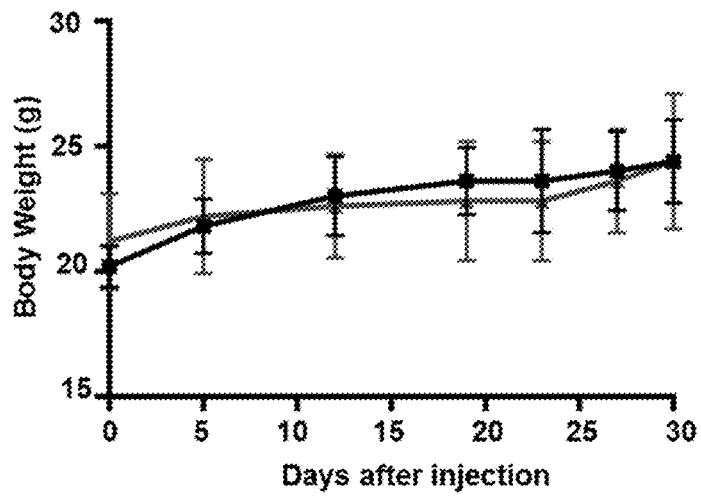
Figure 9C:
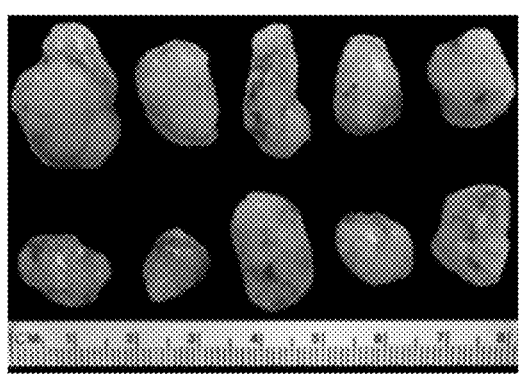
Figure 9D:
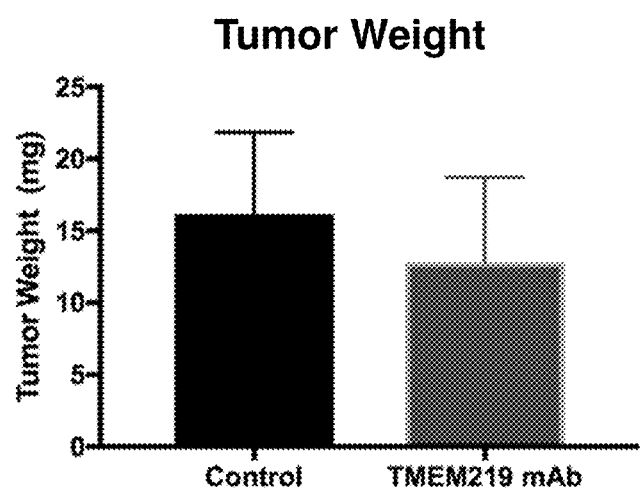

In addition, bioluminescent orthotopic WHIM30 PDX mice showed that administration of a low dose of TMEM219 agonist mAb #274 (1 mg/kg body weight) resulted in tumor shrinkage of up to 29% at day 30 after tumor cell injection (FIG. 9A). No apparent body weight or damage in major organs was observed in TMEM219 agonist mAb administrated mice (FIG. 9B). Consistent with tumor volume data, the size and weight of tumors isolated from TMEM219 agonist mAb administrated mice was significantly reduced compared with those from mouse IgG administrated mice (FIG. 9C). The 25% reduction of tumor weight observed in mAb administered mice was comparable to the 29% tumor shrinkage shown in FIG. 7A. It is noted that these promising antitumor data were obtained from single minimal dose. These results clearly indicate that the TMEM219 anti-tumor signaling pathway is still functional in TNBC and that TMEM219 mAbs represent a new therapeutic intervention for high mortality TNBC.

Colon Cancer (CAC)

An in vivo study was conducted using the Dextran Sulfate Sodium-Azoxymethane (DSS-AOM) mouse model, which is well accepted as a CAC animal model. The results clearly demonstrated that a neutrophil protease inhibitor, al-antitrypsin (AAT) treatment during late-stage CAC resulted in a significant reduction in the frequency and size of tumors in mice harboring established CAC (FIG. 12A-E). Further immunohistochemistry (IHC) data clearly demonstrated significant suppression of intramucosal adenocarcinoma (TIS) formation as well as IL-6, a cell proliferation marker PCNA and a major component of neutrophil azurophilic granules myeloperoxidase (MPO) in colon tissue. In addition, AAT treatment results in a significant increase of TMEM219 agonist in colon tissue as well as in circulation. These data strongly suggests that antitumor effect of AAT may be attributed to reduced TMEM219 natural agonist proteolysis, thereby enhancing TMEM219 natural agonist/TMEM219-mediated antitumor/anti-inflammatory, and further ameliorating neutrophil-activated cytokine function such as activation of the IL-10/IL-6 axis in CAC.

Figure 13A:
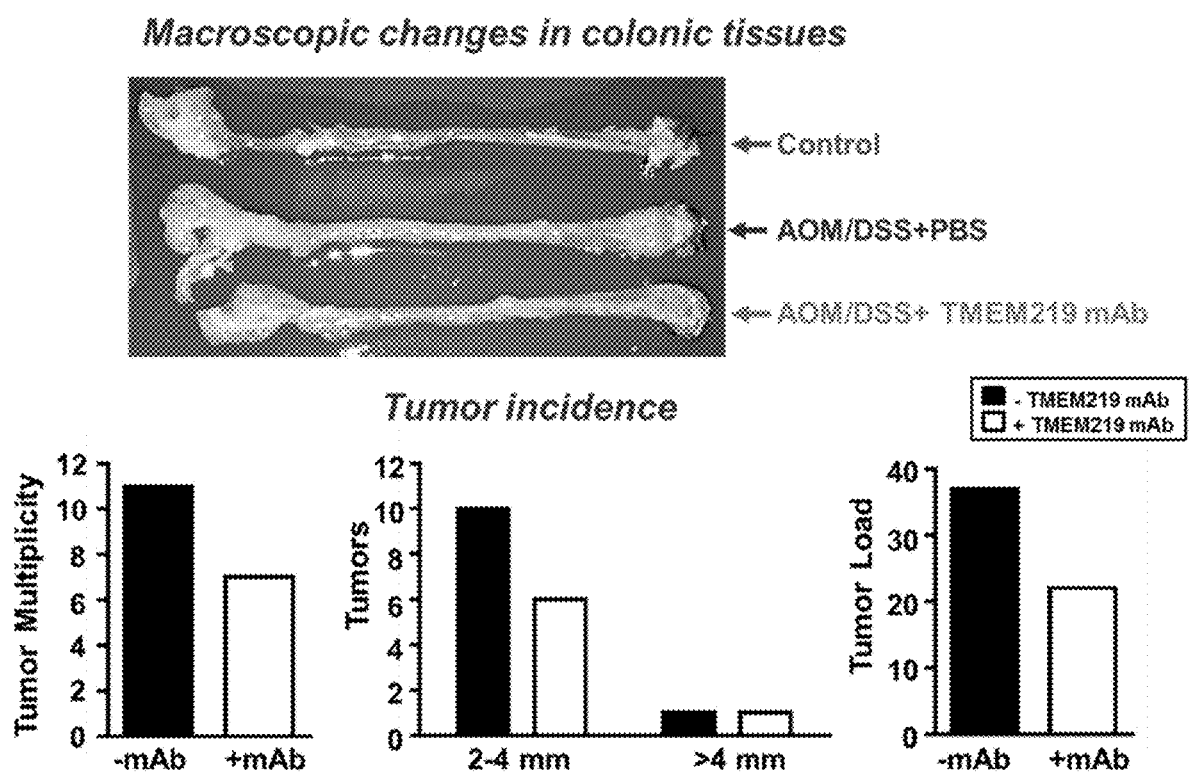
FIG. 13A-C. Antitumor effect of TMEM219 agonist mAb #2 (#274) on colitis-associated colon cancer in the AOM/DSS mouse model (A). Mechanism of action (B and C), TMEM219 mAb #2 (#274) inhibits colon cancer cell growth (B) and TMEM219 mAb #1 (#245) suppresses TNF-alpha-activated inflammatory NF-kappa B signaling in HT-29 colon cancer cells (C).
Figure 13B:
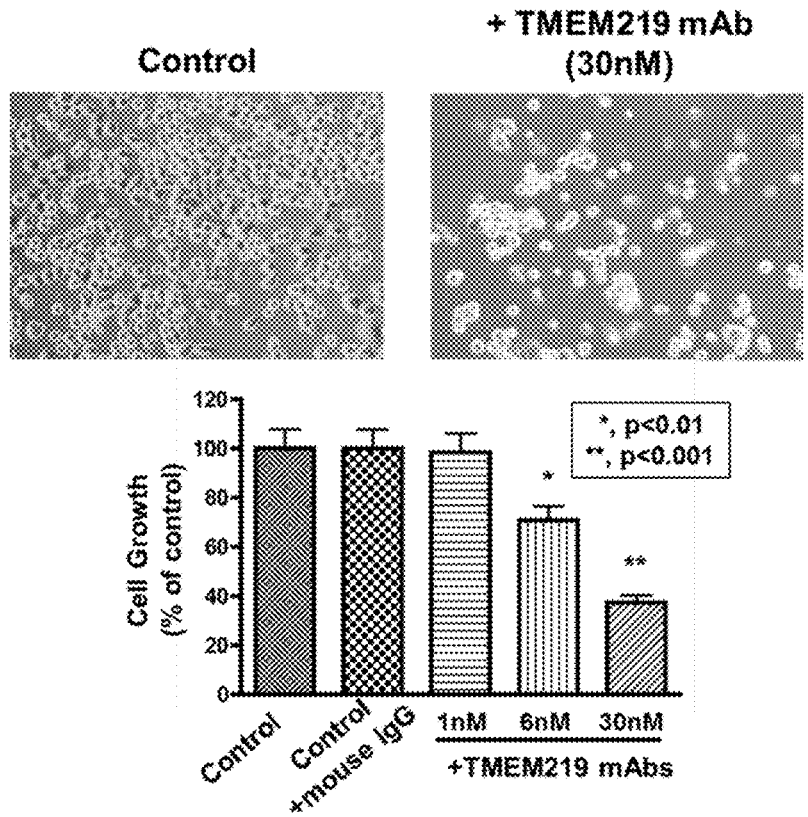
Figure 13C:
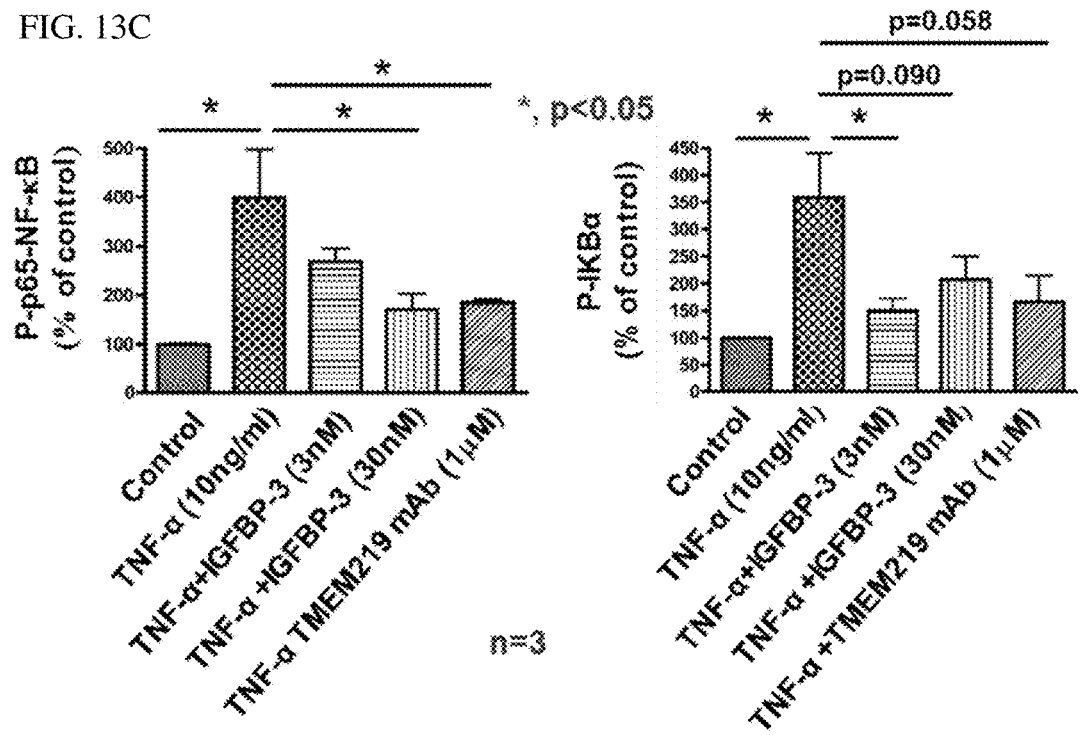

Therapeutic potential of TMEM219 agonist mAbs was further tested for colorectal cancer using an AOM/DSS CAC mouse model. The in vivo preclinical data clearly demonstrate that mice treated with TMEM219 agonist mAb #2 (#274) showed a dramatic suppression of tumor number and size (FIG. 13A). Similarly seen with TMEM219 natural agonist treatment, treatment with TMEM219 agonist mAbs inhibits HT-29 colon cancer cell growth (FIG. 13B) and tumor-activated NF-kappa B signaling as shown decrease of phosphorylated-NF-kappa B and -I kappa B alpha (FIG. 13C).

Lung Cancer

Figure 10:
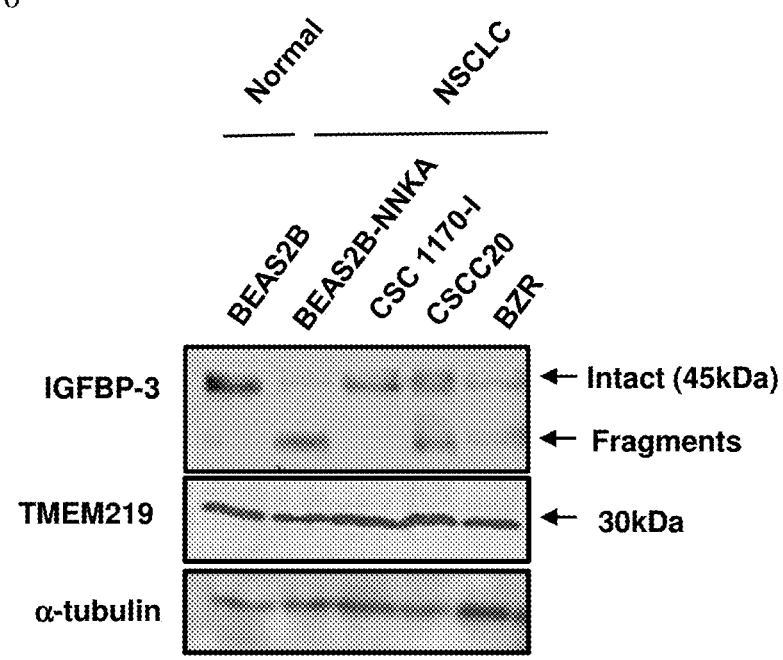
FIG. 10. IGFBP-3/TMEM219 Axis in Normal lung epithelial and NSCLC Cells. TMEM219 is expressed in normal and non-small cell lung carcinoma cells with similar levels. However, expression of IGFBP-3 is significantly suppressed in cancer cells compared to BEAS2B normal lung epithelial cells. More strikingly, IGFBP-3 is proteolyzed in most NSCLC cells except CSCC20 cells.
Figure 11E:
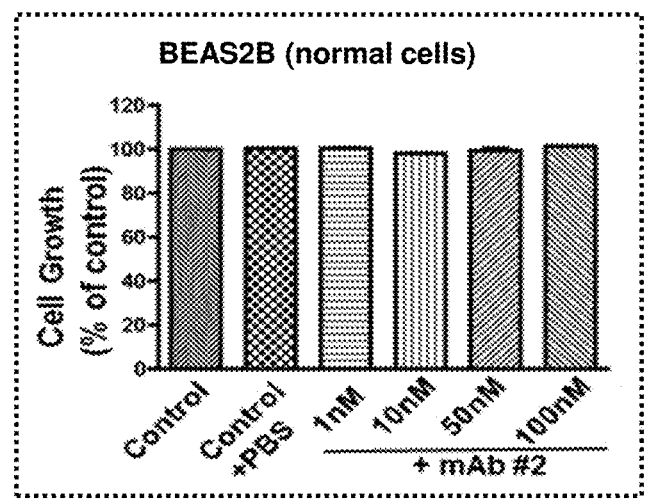
Figure 12A:
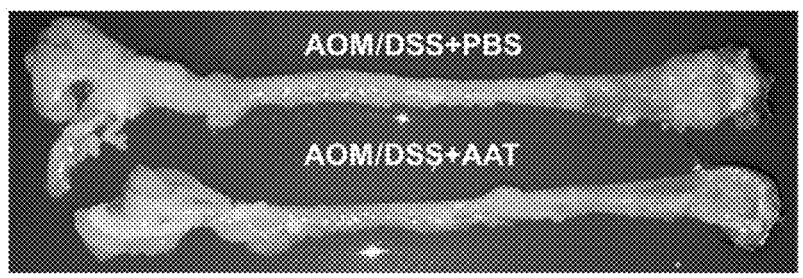
FIG. 12 A-E. Therapeutic potential of AAT on CAC. AAT was treated every 3 days after the last DSS cycle (day 77) for 18 days and tumors were examined on day 98. Macroscopic changes in colonic tissues (A) and tumor incidence (B) * p<0.05, ** p<0.01. Tissue was further processed for hematoxylin/eosin staining (C) and IHC (D). Original magnification 40×, 100× respectively. (E) AAT treatment results in significant inhibition of IGFBP-3 proteolysis in circulation.
Figure 12B:
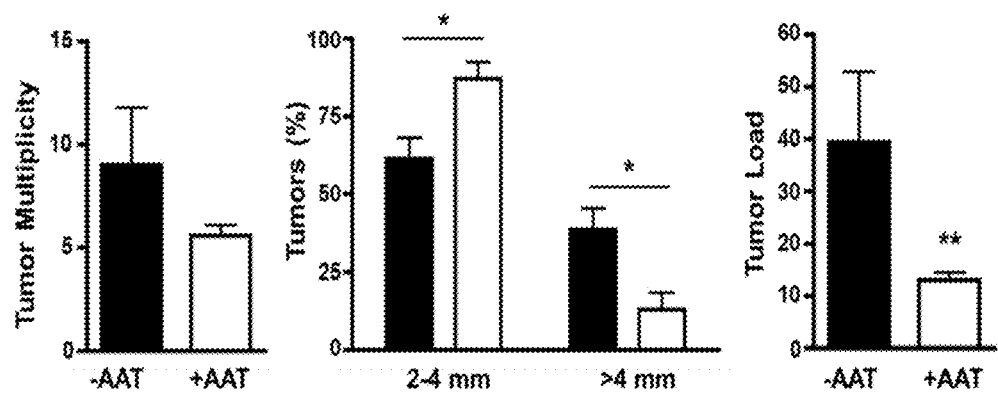
Figure 12C:
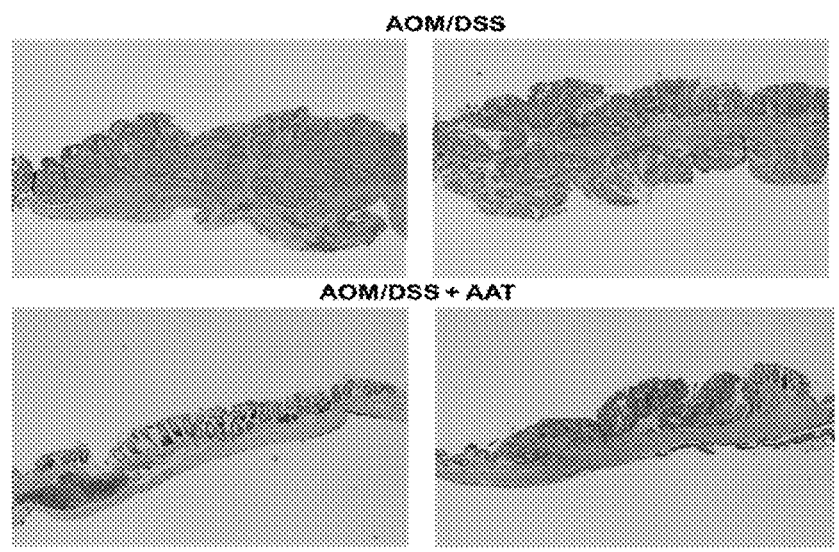
Figure 12D:
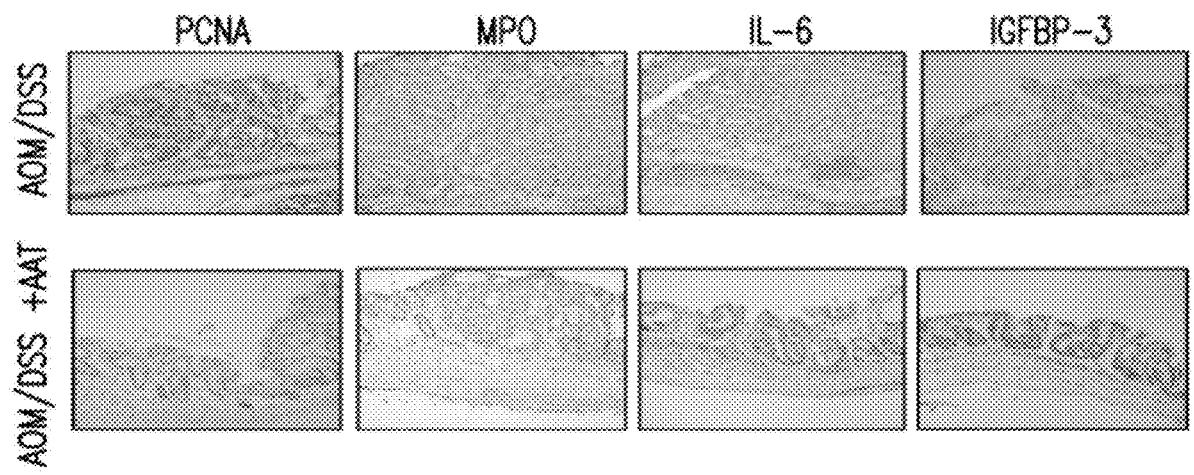
Figure 12E:
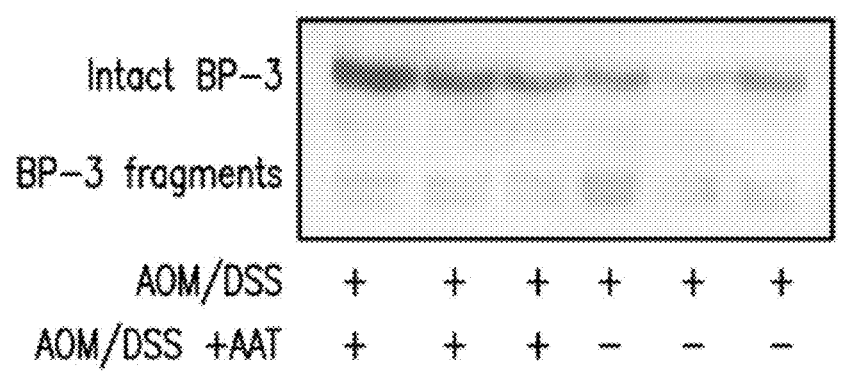

Smoking contributes to 80 percent and 90 percent of lung cancer deaths in women and men, respectively. To date, much evidence exists confirming the involvement of tobacco carcinogens such as NNK in lung tumorigenesis. It is known that, NNK, the most potent tobacco carcinogen, enhances cell proliferation of BEAS-2B, normal lung epithelial cells, and concomitantly suppresses TMEM219 natural agonist but not TMEM219 expression through DNA methylation. Decreased TMEM219 natural agonist expression, and elevated levels of phospho-Akt, phospho-p65-NF-kappaB, and cyclin D1 were detected in tobacco carcinogen-induced tumorigenic derivatives of BEAS-2B. Overexpression of TMEM219 natural agonist in NNKA, one of the derivatives, suppressed NF-kappaB activity and induced apoptosis whereas suppression of TMEM219 with its specific shRNA hindered TMEM219 natural agonist-induced suppression of NF-KB and induction of cell death. These observations indicate that the observed anti-tumor actions of TMEM219 natural agonist is mainly mediated via TMEM219 in NNKA cells. Taken together, this unique tumor specific antiproliferative and proapoptotic property of IGFBP-3/TMEM219 axis provides a strong evidence for its therapeutic value for lung cancer. However, IGFBP-3 itself does not constitute an excellent targeted therapy for lung cancer due to its significant degradation by tumor-induced proteases such as MMPs and ADAM28, thereby attenuating IGFBP-3's antitumor function (FIG. 10). Two TMEM219 mAbs #245 and #274 possess antitumor effects in lung cancer cells but not in normal lung epithelial cells (FIG. 11). In addition, these is findings demonstrate that TMEM219 is a key antitumor signaling and a therapeutic target in NSCLC.

Example 3

According to World Health Organization estimates, overweight and obesity now overshadow underweight and malnutrition as significant causes of premature death. Nearly two-thirds of adults in the United States are overweight or obese, and obesity is a major risk factor for a myriad of serious comorbidities including hypertension, type 2 diabetes mellitus (T2DM), cardiovascular disease (CVD), and other metabolic disorders. Additionally, rapidly increasing rates of obesity in children and young adults has been observed and is resulting in immediate and lifelong metabolic disease risk. Lifestyle changes to counteract obesity and physical inactivity have been emphasized as the first line of defense against progression to T2DM, however there has been no significant decrease in the incidence of obesity. More effective preventive and therapeutic strategies are needed to thwart obesity and associated metabolic complications.

Insulin resistance (IR) represents a common metabolic derangement that contributes to the development of many obesity-related comorbidities including T2DM. Although it is generally established that low-grade adipose tissue inflammation contributes substantially to the burden of IR, the pathophysiology underlying the development of IR is complex and multifactorial. Thus, a clearer understanding of the mechanisms leading to obesity-associated IR is necessary to identify novel targets for the prevention and treatment of many IR-driven conditions such as T2DM. The endocrine paradigm suggests that visceral fat in obesity, consisting primarily of adipocytes, secretes various pro-inflammatory adipokines such as tumor necrosis factor (TNF), leptin, visfatin, resistin, and interleukin (IL)-6 creating a state of local thus accelerating events leading to systemic IR, T2DM and metabolic syndrome. Recent studies have further identified that obesity-induced inflammatory adipokines/cytokines interfere with insulin signaling in visceral adipocytes by decreasing the levels of insulin receptor substrate-1 (IRS-1), glucose transporter-4 (GLUT4) and adiponectin leading to a state of IR via autocrine/paracrine influences.

IGFBP-3 inhibits TNF-alpha-induced NF-kappa B activity through IGFBP-3R, thereby restoring insulin signaling and negating TNF-alpha-induced inhibition of glucose uptake in human primary adipocytes, suggesting that the IGFBP-3/IGFBP-3R system plays an important role in cytokine/adipokine-induced IR in visceral adipocytes. Furthermore, there is a decrease in functional intact IGFBP-3 levels and an increase in IGFBP-3 degradation (proteolysis) in the circulation of overweight and obese adolescents when compared with their non-obese counterpart. Moreover, a significant inverse correlation is observed between functional IGFBP-3 and adiposity parameters such as waist circumference, body mass index and homeostasis model assessment of insulin resistance (HOMA-IR). These findings suggest that inflammation-induced decrease of intact IGFBP-3 due to decreased IGFBP-3 production as well as increased IGFBP-3 degradation (proteolysis) in overweight and obese population likely results in reduced levels of functional IGFBP-3 in circulation, effectively blunting the anti-inflammatory and insulin-sensitizing functions of the IGFBP-3/IGFBP-3R system in adipose tissue. It further suggests a regulatory role for the IGFBP-3/IGFBP-3R system in glucose homeostasis.

Figure 14A:
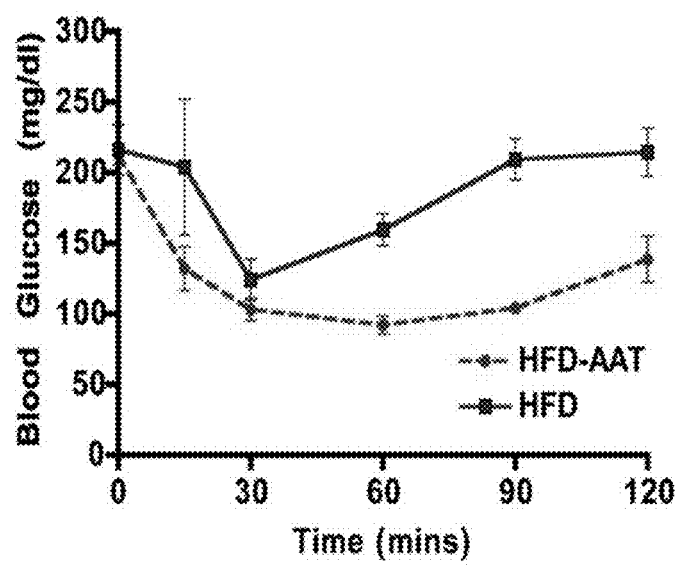
FIG. 14A-C. HFD fed mice with AAT administration results in increase of insulin sensitivity and decrease IGFBP-3 proteolysis accompanying reduced hepatic lipogenesis and inflammation in visceral fat. A, Insulin tolerance test in HFD-fed mice treated with or without AAT weekly (60 mg/kg body weight) for 7 weeks. Mice were fasted for 6h (n=3 per group) before the ITT. B, H & E staining of liver (A,C) and visceral fat (B,D) with or without AAT for 7 weeks. B, AAT treatment results in reduction in fatty liver and infiltration of monocytes in visceral fat. C, Serum IGFBP-3 proteolysis levels (ratio of IGFBP-3 fragment over total IGFBP-3) in HFD-fed mice treated with or without AAT for 7 weeks. * P<0.05.
Figure 14B:
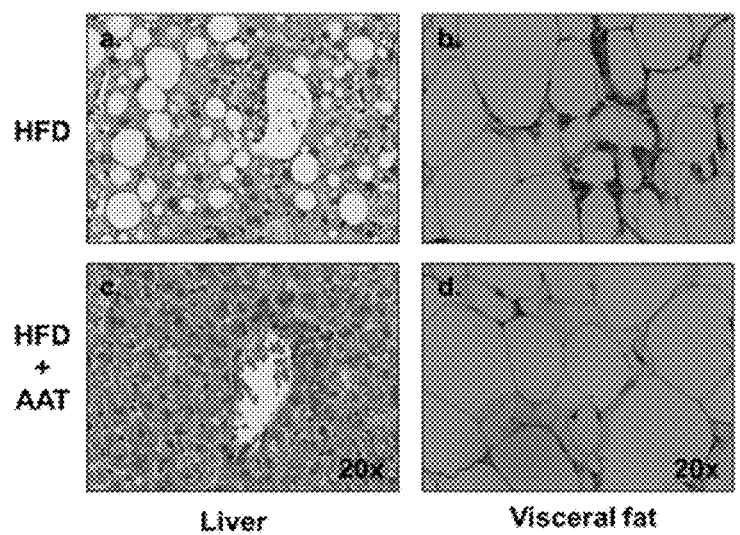
Figure 14C:
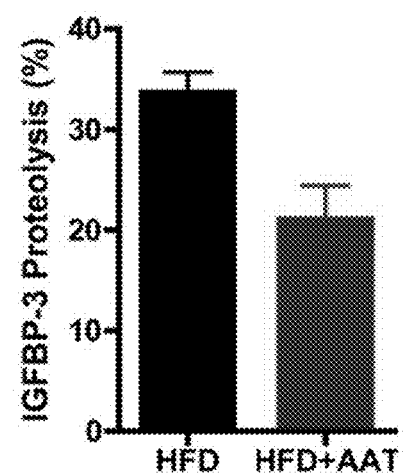

An in vivo study using Aralast (a clinical formulation of human Alpha1-Proteinase Inhibitor, "AAT") using a diet-induced obese (DIO) mouse model showed that mice fed with high fat diet (HFD) for 15 weeks resulted in a significant insulin resistance (IR) shown by ITT whereas AAT treated HFD mice showed a significant improvement in IR (FIG. 14A). In addition, H&E staining of liver and visceral fat tissues demonstrated that AAT reduced hepatic steatosis and visceral fat inflammation (FIG. 14B). Furthermore, a significant decrease of serum IGFBP-3 proteolysis was observed in AAT administrated HFD mice. (FIG. 14C). These in vivo data clearly indicates therapeutic potential of AAT and TMEM219 agonists (IGFBP-3 and TMEM219 agonist antibodies).

Figure 15:
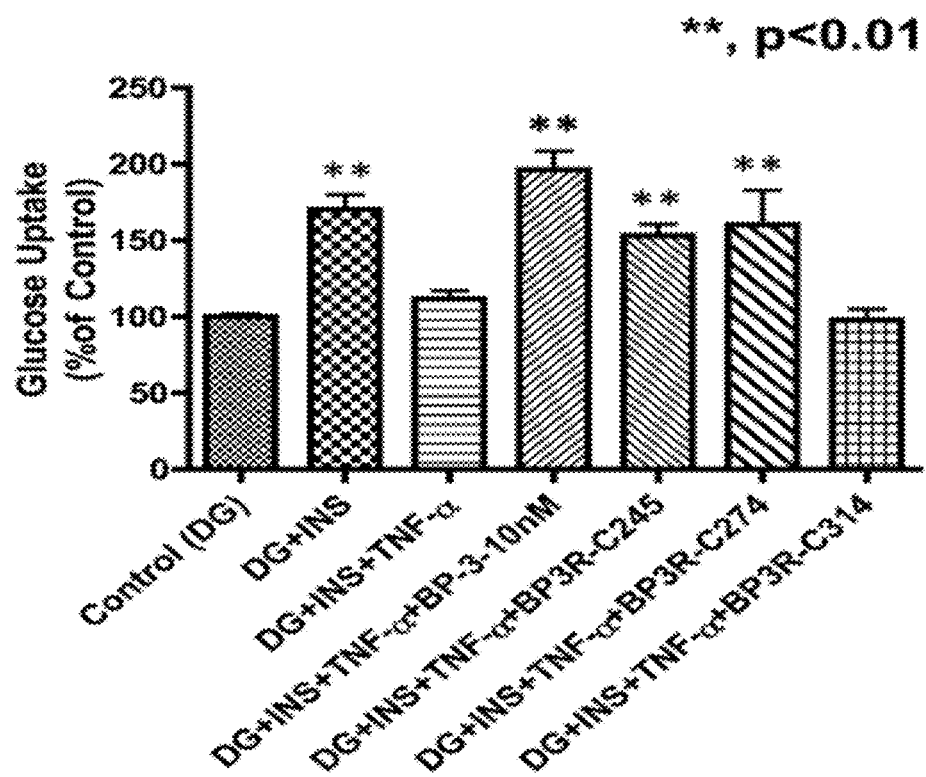
FIG. 15. TMEM219 mediates IGFBP-3-induced insulin sensitizing function. IGFBP-3 agonist monoclonal Abs (#245 and #274) but not non-agonist mAb (C314) inhibit TNF-α-induced suppression of glucose uptake in primary human adipocytes. n=3, in duplicate; **, p<0.01

In order to identify the functional significance and therapeutic potential of IGFBP-3R agonistic antibodies in IGFBP-3-induced anti-inflammatory and insulin sensitizing effects studies were conducted in which IGFBP-3R agonist mAbs #245 and #274 and non-agonistic IGFBP-3R monoclonal antibodies (#C314) were employed in the presence of insulin and TNF-alpha in fully differentiated adipocytes. As shown in FIG. 15, IGFBP-3R agonist mAbs #245 and #274, but not non-agonistic mAb, restored TNF-alpha-induced inhibition of glucose uptake in primary adipocytes. These results show that IGFBP-3R agonist mAbs inhibit TNF-α-induced insulin resistance by inhibiting TNF-alpha-induced NF-kappa B activity in adipocytes.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

The invention claimed is:

1. An antibody that binds to and activates the insulin-like growth factor-binding protein 3 receptor (IGFBP-3R), wherein the antibody contains the complementarity determining regions (CDRs) SEQ ID NO: 15, SEQ ID NO: 17, SEQ ID NO: 19, SEQ ID NO: 21, SEQ ID NO: 23, and the amino acid sequence ATS.

2. The antibody of claim 1, wherein the antibody comprises a detectable label.

3. A method of treating an IGFBP-3R expressing cancer in a patient in need thereof, comprising:
administering to said patient a therapeutically effective amount of an antibody that binds to and activates the insulin-like growth factor-binding protein 3 receptor (IGFBP-3R), wherein the antibody contains the CDRs SEQ ID NO: 15, SEQ ID NO: 17, SEQ ID NO: 19, SEQ ID NO: 21, SEQ ID NO: 23, and the amino acid sequence ATS.

4. The method of claim 3, wherein said IGFBP-3R expressing cancer is breast cancer, colon cancer, lung cancer, ovarian cancer, pancreatic cancer, liver cancer, head and neck cancer, prostate cancer or a liquid tumor.

5. The method of claim 4, wherein the liquid tumor is a leukemia.

* * * * *

SEQUENCE LISTING

<160> NUMBER OF SEQ ID NOS: 33

<210> SEQ ID NO 1
<211> LENGTH: 352
<212> TYPE: DNA
<213> ORGANISM: Artificial Sequence
<220> FEATURE:
<223> OTHER INFORMATION: Synthetic antibody

<400> SEQUENCE: 1

```
cagatccagt tggtgcagtc tggacctgag ctgaaggagc ctggagagac agtcaagatc      60
tcctgcaagg cttctgggta tactttcaca aactatggaa tgaactgggt gaagcaggct     120
ccaggaaggg tttaaagtgg atgggctgga taaacaccta caccagagag acaacatata     180
ttgatgagtt caagggacgg tctgccttct ctatggaaac ctctgccagc actgcctatt     240
tgcagatcta caactcaaaa atgaggacac ggctacatat ttctgtgcaa gagggtctac     300
gatgtatggt ctggacaagt ggggtcaagg aacctcagtc accgtctcct ca             352
```

<210> SEQ ID NO 2
<211> LENGTH: 118
<212> TYPE: PRT
<213> ORGANISM: Artificial Sequence
<220> FEATURE:
<223> OTHER INFORMATION: Synthetic antibody

<400> SEQUENCE: 2

```
Gln Ile Gln Leu Val Gln Ser Gly Pro Glu Leu Lys Glu Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45
```

```
Gly Trp Ile Asn Thr Tyr Thr Arg Glu Thr Thr Tyr Ile Asp Glu Phe
 50                  55                  60

Lys Gly Arg Ser Ala Phe Ser Met Glu Thr Ser Ala Ser Thr Ala Tyr
 65                  70                  75                  80

Leu Gln Ile Tyr Asn Leu Lys Asn Glu Asp Thr Ala Thr Tyr Phe Cys
                 85                  90                  95

Ala Arg Gly Ser Thr Met Tyr Gly Leu Asp Lys Trp Gly Gln Gly Thr
            100                 105                 110

Ser Val Thr Val Ser Ser
        115

<210> SEQ ID NO 3
<211> LENGTH: 322
<212> TYPE: DNA
<213> ORGANISM: Artificial Sequence
<220> FEATURE:
<223> OTHER INFORMATION: Synthetic antibody

<400> SEQUENCE: 3
gacattgtga tgacccagtc tcaaaaattc atgtccacat cagtgggaga cggggtcagc    60
gtcacctgta aggccagtca gaatgtgggt actaatgtag tctggtatca acagaaacca   120
gggcaattcc taaggcactg atttactcgg catcctaccg gtacagtgga gtccctgatc   180
gcttcacagg cagtggatct gggacagatt tcactctcac catcagcaat gtgcagtctg   240
aagacttggc agaaatttct gtcaccaata taacagctat cctctcacgt tcggtgctgg   300
gaccaagctg gagctgaaac gg                                            322

<210> SEQ ID NO 4
<211> LENGTH: 108
<212> TYPE: PRT
<213> ORGANISM: Artificial Sequence
<220> FEATURE:
<223> OTHER INFORMATION: Synthetic antibody

<400> SEQUENCE: 4

Asp Ile Val Met Thr Gln Ser Gln Lys Phe Met Ser Thr Ser Val Gly
 1               5                  10                  15

Asp Gly Val Ser Val Thr Cys Lys Ala Ser Gln Asn Val Gly Thr Asn
             20                  25                  30

Val Val Trp Tyr Gln Gln Lys Pro Gly Gln Ser Pro Lys Ala Leu Ile
         35                  40                  45

Tyr Ser Ala Ser Tyr Arg Tyr Ser Gly Val Pro Asp Arg Phe Thr Gly
 50                  55                  60

Ser Gly Ser Gly Thr Asp Phe Thr Leu Thr Ile Ser Asn Val Gln Ser
 65                  70                  75                  80

Glu Asp Leu Ala Glu Tyr Phe Cys His Gln Tyr Asn Ser Tyr Pro Leu
                 85                  90                  95

Thr Phe Gly Ala Gly Thr Lys Leu Glu Leu Lys Arg
            100                 105

<210> SEQ ID NO 5
<211> LENGTH: 354
<212> TYPE: DNA
<213> ORGANISM: Artificial Sequence
<220> FEATURE:
<223> OTHER INFORMATION: Synthetic antibody

<400> SEQUENCE: 5
```

```
cagatccagt tggtgcagtc tggacctgag ctgaaggagc tggagagaca gtcaagatc      60 tcctgcaagg cttctgggta tactttcaca aactatggaa tgaactgggt gaagcaggct    120
ccaggaaagg gtttaaagtg gatgggctgg ataaacacct acaccagaga gacaacatat    180
attgatgagt tcaagggacg gtctgccttc tctatggaaa cctctgccag cactgcctat    240
ttgcagatct acaacctcaa aaatgaggac acggctacat atttctgtgc aagagggtct    300
acgatgtatg gtctggacaa gtggggtcaa ggaacctcag tcaccgtctc ctca           354
```

<210> SEQ ID NO 6
<211> LENGTH: 118
<212> TYPE: PRT
<213> ORGANISM: Artificial Sequence
<220> FEATURE:
<223> OTHER INFORMATION: Synthetic antibody

<400> SEQUENCE: 6

```
Gln Ile Gln Leu Val Gln Ser Gly Pro Glu Leu Lys Glu Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Arg Glu Thr Thr Tyr Ile Asp Glu Phe
    50                  55                  60

Lys Gly Arg Ser Ala Phe Ser Met Glu Thr Ser Ala Ser Thr Ala Tyr
65                  70                  75                  80

Leu Gln Ile Tyr Asn Leu Lys Asn Glu Asp Thr Ala Thr Tyr Phe Cys
                85                  90                  95

Ala Arg Gly Ser Thr Met Tyr Gly Leu Asp Lys Trp Gly Gln Gly Thr
            100                 105                 110

Ser Val Thr Val Ser Ser
        115
```

<210> SEQ ID NO 7
<211> LENGTH: 324
<212> TYPE: DNA
<213> ORGANISM: Artificial Sequence
<220> FEATURE:
<223> OTHER INFORMATION: Synthetic antibody

<400> SEQUENCE: 7

```
gacattgtga tgacccagtc tcaaaaattc atgtccacat cagtgggaga cggggtcagc     60
gtcacctgta aggccagtca gaatgtgggt actaatgtag tctggtatca acagaaacca    120
gggcaatctc ctaaggcact gatttactcg gcatcctacc ggtacagtgg agtccctgat    180
cgcttcacag gcagtggatc tgggacagat ttcactctca ccatcagcaa tgtgcagtct    240
gaagacttgg cagaatattt ctgtcaccaa tataacagct atcctctcac gttcggtgct    300
gggaccaagc tggagctgaa acgg                                           324
```

<210> SEQ ID NO 8
<211> LENGTH: 108
<212> TYPE: PRT
<213> ORGANISM: Artificial Sequence
<220> FEATURE:
<223> OTHER INFORMATION: Synthetic antibody

<400> SEQUENCE: 8

Asp Ile Val Met Thr Gln Ser Gln Lys Phe Met Ser Thr Ser Val Gly

```
1               5                  10                 15
Asp Gly Val Ser Val Thr Cys Lys Ala Ser Gln Asn Val Gly Thr Asn
                20                 25                 30
Val Val Trp Tyr Gln Gln Lys Pro Gly Gln Ser Pro Lys Ala Leu Ile
                35                 40                 45
Tyr Ser Ala Ser Tyr Arg Tyr Ser Gly Val Pro Asp Arg Phe Thr Gly
                50                 55                 60
Ser Gly Ser Gly Thr Asp Phe Thr Leu Thr Ile Ser Asn Val Gln Ser
 65                 70                 75                 80
Glu Asp Leu Ala Glu Tyr Phe Cys His Gln Tyr Asn Ser Tyr Pro Leu
                85                 90                 95
Thr Phe Gly Ala Gly Thr Lys Leu Glu Leu Lys Arg
               100                105
```

```
<210> SEQ ID NO 9
<211> LENGTH: 1419
<212> TYPE: DNA
<213> ORGANISM: Artificial Sequence
<220> FEATURE:
<223> OTHER INFORMATION: Synthetic antibody

<400> SEQUENCE: 9
atggacccca agggcagcct gagctggaga atcctgctgt tcctgagcct ggccttcgag    60
ctgagctacg ccagatcca gttggtgcag tctggacctg agctgaagga gcctggagag   120
acagtcaaga tctcctgcaa ggcttctggg tatactttca caaactatgg aatgaactgg   180
gtgaagcagg ctccaggaaa gggtttaaag tggatgggct ggataaacac ctacaccaga   240
gagacaacat atattgatga gttcaaggga cggtctgcct tctctatgga aacctctgcc   300
agcactgcct atttgcagat ctacaacctc aaaaatgagg acacggctac atatttctgt   360
gcaagagggt ctacgatgta tggtctggac aagtggggtc aaggaacctc agtcaccgtc   420
tcctcagcta gcaccaaggg cccagcgtg ttccctctgg cccccagcag caagagcacc   480
agcggcggaa ccgccgccct gggctgcctg gtgaaggact acttccccga gccgtgacc   540
gtgtcctgga cagcggcgc tctgaccagc ggagtgcaca ccttccctgc cgtgctgcag   600
agcagcggcc tgtactccct gagcagcgtg gtgaccgtgc ccagcagcag cctgggcacc   660
cagacctaca tctgcaacgt gaaccacaag ccctccaaca ccaaggtgga caagaaggtg   720
gagcctaaga gctgcgacaa gacccacacc tgccctccct gccccgcccc cgagctgctg   780
ggcggaccca gcgtgttcct gttccctccc aagcccaagg acaccctgat gatcagccgc   840
acccccgagg tgacctgcgt ggtggtggac gtgagccacg aggaccccga ggtgaagttc   900
aactggtacg tggacggcgt ggaggtgcac aacgccaaga ccaagcctcg ggaggagcag   960
tacaactcca cctaccgcgt ggtgagcgtg ctgaccgtgc tgcaccagga ctggctgaac  1020
ggcaaggagt acaagtgcaa ggtgagcaac aaggccctgc cgctcccat cgagaagacc  1080
atcagcaagg ccaagggcca gccccgggag cctcaggtgt acaccctgcc cccagccgc  1140
gacgagctga ccaagaacca ggtgagcctg acctgcctgg tgaagggctt ctacccctcc  1200
gacatcgccg tggagtggga gagcaacggc cagcctgaga caactacaa gaccacccct  1260
cccgtgctgg acagcgacgg cagcttcttc ctgtacagca agctgaccgt ggacaagtcc  1320
cggtggcagc agggcaacgt gttcagctgc agcgtgatgc acgaggccct gcacaaccac  1380
tacacccaga agagcctgag cctgagcccc ggatagtaa                         1419
```

<210> SEQ ID NO 10
<211> LENGTH: 471
<212> TYPE: PRT
<213> ORGANISM: Artificial Sequence
<220> FEATURE:
<223> OTHER INFORMATION: Synthetic antibody

<400> SEQUENCE: 10

```
Met Asp Pro Lys Gly Ser Leu Ser Trp Arg Ile Leu Leu Phe Leu Ser
1               5                   10                  15

Leu Ala Phe Glu Leu Ser Tyr Gly Gln Ile Gln Leu Val Gln Ser Gly
            20                  25                  30

Pro Glu Leu Lys Glu Pro Gly Glu Thr Val Lys Ile Ser Cys Lys Ala
        35                  40                  45

Ser Gly Tyr Thr Phe Thr Asn Tyr Gly Met Asn Trp Val Lys Gln Ala
    50                  55                  60

Pro Gly Lys Gly Leu Lys Trp Met Gly Trp Ile Asn Thr Tyr Thr Arg
65                  70                  75                  80

Glu Thr Thr Tyr Ile Asp Glu Phe Lys Gly Arg Ser Ala Phe Ser Met
                85                  90                  95

Glu Thr Ser Ala Ser Thr Ala Tyr Leu Gln Ile Tyr Asn Leu Lys Asn
            100                 105                 110

Glu Asp Thr Ala Thr Tyr Phe Cys Ala Arg Gly Ser Thr Met Tyr Gly
        115                 120                 125

Leu Asp Lys Trp Gly Gln Gly Thr Ser Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
```

```
                370               375               380
Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
                420                 425                 430

Ser Lys Leu Thr Val Asp Lys Ser Arg Trp Gln Gln Gly Asn Val Phe
            435                 440                 445

Ser Cys Ser Val Met His Glu Ala Leu His Asn His Tyr Thr Gln Lys
            450                 455                 460

Ser Leu Ser Leu Ser Pro Gly
465                 470

<210> SEQ ID NO 11
<211> LENGTH: 705
<212> TYPE: DNA
<213> ORGANISM: Artificial Sequence
<220> FEATURE:
<223> OTHER INFORMATION: Synthetic antibody

<400> SEQUENCE: 11
atggagaccg acaccctgct gctctgggtg ctgctgctct gggtgcccgg ctccaccgga      60
gacattgtga tgacccagtc tcaaaaattc atgtccacat cagtgggaga cggggtcagc     120
gtcacctgta aggccagtca gaatgtgggt actaatgtag tctggtatca acagaaacca     180
gggcaatctc ctaaggcact gatttactcg gcatcctacc ggtacagtgg agtccctgat     240
cgcttcacag gcagtggatc tgggacagat ttcactctca ccatcagcaa tgtgcagtct     300
gaagacttgg cagaatattt ctgtcaccaa tataacagct atcctctcac gttcggtgct     360
gggaccaagc tggagctgaa acggaccgtg gccgccccca gcgtgttcat cttccctccc     420
agcgacgagc agctgaagtc tggcaccgcc agcgtggtgt gcctgctgaa caacttctac     480
ccccgcgagg ccaaggtgca gtggaaggtg gacaacgccc tgcagagcgg caacagccag     540
gagagcgtga ccgagcagga ctccaaggac agcacctaca gcctgagcag caccctgacc     600
ctgagcaagg ccgactacga gaagcacaag gtgtacgcct gcgaggtgac ccaccaggga     660
ctgtctagcc ccgtgaccaa gagcttcaac cggggcgagt gctaa                     705

<210> SEQ ID NO 12
<211> LENGTH: 234
<212> TYPE: PRT
<213> ORGANISM: Artificial Sequence
<220> FEATURE:
<223> OTHER INFORMATION: Synthetic antibody

<400> SEQUENCE: 12

Met Glu Thr Asp Thr Leu Leu Leu Trp Val Leu Leu Leu Trp Val Pro
1               5                   10                  15

Gly Ser Thr Gly Asp Ile Val Met Thr Gln Ser Gln Lys Phe Met Ser
                20                  25                  30

Thr Ser Val Gly Asp Gly Val Ser Val Thr Cys Lys Ala Ser Gln Asn
            35                  40                  45

Val Gly Thr Asn Val Val Trp Tyr Gln Gln Lys Pro Gly Gln Ser Pro
        50                  55                  60

Lys Ala Leu Ile Tyr Ser Ala Ser Tyr Arg Tyr Ser Gly Val Pro Asp
65                  70                  75                  80
```

```
Arg Phe Thr Gly Ser Gly Ser Gly Thr Asp Phe Thr Leu Thr Ile Ser
                85                  90                  95
Asn Val Gln Ser Glu Asp Leu Ala Glu Tyr Phe Cys His Gln Tyr Asn
            100                 105                 110
Ser Tyr Pro Leu Thr Phe Gly Ala Gly Thr Lys Leu Glu Leu Lys Arg
        115                 120                 125
Thr Val Ala Ala Pro Ser Val Phe Ile Phe Pro Pro Ser Asp Glu Gln
    130                 135                 140
Leu Lys Ser Gly Thr Ala Ser Val Val Cys Leu Leu Asn Asn Phe Tyr
145                 150                 155                 160
Pro Arg Glu Ala Lys Val Gln Trp Lys Val Asp Asn Ala Leu Gln Ser
                165                 170                 175
Gly Asn Ser Gln Glu Ser Val Thr Glu Gln Asp Ser Lys Asp Ser Thr
            180                 185                 190
Tyr Ser Leu Ser Ser Thr Leu Thr Leu Ser Lys Ala Asp Tyr Glu Lys
        195                 200                 205
His Lys Val Tyr Ala Cys Glu Val Thr His Gln Gly Leu Ser Ser Pro
    210                 215                 220
Val Thr Lys Ser Phe Asn Arg Gly Glu Cys
225                 230
```

<210> SEQ ID NO 13
<211> LENGTH: 10
<212> TYPE: PRT
<213> ORGANISM: Artificial Sequence
<220> FEATURE:
<223> OTHER INFORMATION: Synthetic peptide

<400> SEQUENCE: 13

```
Gly Leu Lys Gly Ser Ser Ala Gly Gln Leu
1               5                   10
```

<210> SEQ ID NO 14
<211> LENGTH: 24
<212> TYPE: DNA
<213> ORGANISM: Artificial Sequence
<220> FEATURE:
<223> OTHER INFORMATION: Synthetic CDR sequence

<400> SEQUENCE: 14
gggtttacct tcacatacta tgga                                          24

<210> SEQ ID NO 15
<211> LENGTH: 8
<212> TYPE: PRT
<213> ORGANISM: Artificial Sequence
<220> FEATURE:
<223> OTHER INFORMATION: Synthetic CDR sequence

<400> SEQUENCE: 15

```
Gly Phe Thr Phe Thr Tyr Tyr Gly
1               5
```

<210> SEQ ID NO 16
<211> LENGTH: 24
<212> TYPE: DNA
<213> ORGANISM: Artificial Sequence
<220> FEATURE:
<223> OTHER INFORMATION: Synthetic CDR sequence

<400> SEQUENCE: 16
ataaacacct acactggaga gcca                                          24

<210> SEQ ID NO 17
<211> LENGTH: 8
<212> TYPE: PRT
<213> ORGANISM: Artificial Sequence
<220> FEATURE:
<223> OTHER INFORMATION: Synthetic CDR sequence

<400> SEQUENCE: 17

Ile Asn Thr Tyr Thr Gly Glu Pro
1               5

<210> SEQ ID NO 18
<211> LENGTH: 33
<212> TYPE: DNA
<213> ORGANISM: Artificial Sequence
<220> FEATURE:
<223> OTHER INFORMATION: Synthetic CDR sequence

<400> SEQUENCE: 18
gcaagagggc gtacggtagt gggctttgac tct                                  33

<210> SEQ ID NO 19
<211> LENGTH: 11
<212> TYPE: PRT
<213> ORGANISM: Artificial Sequence
<220> FEATURE:
<223> OTHER INFORMATION: Synthetic CDR sequence

<400> SEQUENCE: 19

Ala Arg Gly Arg Thr Val Val Gly Phe Asp Ser
1               5                   10

<210> SEQ ID NO 20
<211> LENGTH: 18
<212> TYPE: DNA
<213> ORGANISM: Artificial Sequence
<220> FEATURE:
<223> OTHER INFORMATION: Synthetic CDR sequence

<400> SEQUENCE: 20
caggacattg gtagtagc                                                   18

<210> SEQ ID NO 21
<211> LENGTH: 6
<212> TYPE: PRT
<213> ORGANISM: Artificial Sequence
<220> FEATURE:
<223> OTHER INFORMATION: Synthetic CDR sequence

<400> SEQUENCE: 21

Gln Asp Ile Gly Ser Ser
1               5

<210> SEQ ID NO 22
<211> LENGTH: 27
<212> TYPE: DNA
<213> ORGANISM: Artificial Sequence
<220> FEATURE:
<223> OTHER INFORMATION: Synthetic CDR sequence

<400> SEQUENCE: 22
ctacaatatg ctagttctcc gtacacg                                         27

<210> SEQ ID NO 23
<211> LENGTH: 7

```
<212> TYPE: PRT
<213> ORGANISM: Artificial Sequence
<220> FEATURE:
<223> OTHER INFORMATION: Synhetic CDR sequence

<400> SEQUENCE: 23

Leu Gln Tyr Ala Ser Ser Pro
1               5

<210> SEQ ID NO 24
<211> LENGTH: 24
<212> TYPE: DNA
<213> ORGANISM: Artificial Sequence
<220> FEATURE:
<223> OTHER INFORMATION: Synthetic CDR sequence

<400> SEQUENCE: 24
gggtatactt tcacaaacta tgga                                              24

<210> SEQ ID NO 25
<211> LENGTH: 8
<212> TYPE: PRT
<213> ORGANISM: Artificial Sequence
<220> FEATURE:
<223> OTHER INFORMATION: Synthetic CDR sequence

<400> SEQUENCE: 25

Gly Tyr Thr Phe Thr Asn Tyr Gly
1               5

<210> SEQ ID NO 26
<211> LENGTH: 24
<212> TYPE: DNA
<213> ORGANISM: Artificial Sequence
<220> FEATURE:
<223> OTHER INFORMATION: Syntehtic CDR sequence

<400> SEQUENCE: 26
ataaacacct acaccagaga gaca                                              24

<210> SEQ ID NO 27
<211> LENGTH: 8
<212> TYPE: PRT
<213> ORGANISM: Artificial Sequence
<220> FEATURE:
<223> OTHER INFORMATION: Synthetic CDR sequence

<400> SEQUENCE: 27

Ile Asn Thr Tyr Thr Arg Glu Thr
1               5

<210> SEQ ID NO 28
<211> LENGTH: 33
<212> TYPE: DNA
<213> ORGANISM: Artificial Sequence
<220> FEATURE:
<223> OTHER INFORMATION: Synthetic CDR sequence

<400> SEQUENCE: 28
gcaagagggt ctacgatgta tggtctggac aag                                    33

<210> SEQ ID NO 29
<211> LENGTH: 11
<212> TYPE: PRT
<213> ORGANISM: Artificial Sequence
<220> FEATURE:
<223> OTHER INFORMATION: Synthetic CDR sequence
```

<400> SEQUENCE: 29

Ala Arg Gly Ser Thr Met Tyr Gly Leu Asp Lys
1               5                   10

<210> SEQ ID NO 30
<211> LENGTH: 18
<212> TYPE: DNA
<213> ORGANISM: Artificial Sequence
<220> FEATURE:
<223> OTHER INFORMATION: Synthetic CDR sequence

<400> SEQUENCE: 30
cagaatgtgg gtactaat                                          18

<210> SEQ ID NO 31
<211> LENGTH: 6
<212> TYPE: PRT
<213> ORGANISM: Artificial Sequence
<220> FEATURE:
<223> OTHER INFORMATION: Synthetic CDR sequence

<400> SEQUENCE: 31

Gln Asn Val Gly Thr Asn
1               5

<210> SEQ ID NO 32
<211> LENGTH: 27
<212> TYPE: DNA
<213> ORGANISM: Artificial Sequence
<220> FEATURE:
<223> OTHER INFORMATION: Synthetic CDR sequence

<400> SEQUENCE: 32
caccaatata acagctatcc tctcacg                                27

<210> SEQ ID NO 33
<211> LENGTH: 9
<212> TYPE: PRT
<213> ORGANISM: Artificial Sequence
<220> FEATURE:
<223> OTHER INFORMATION: Synthetic CDR sequence

<400> SEQUENCE: 33

His Gln Tyr Asn Ser Tyr Pro Leu Thr
1               5